(12) United States Patent
Schröder et al.

(10) Patent No.: US 6,436,681 B1
(45) Date of Patent: Aug. 20, 2002

(54) METHOD FOR PRODUCING BIOTIN

(75) Inventors: Hartwig Schröder, Nussloch; Bernhard Hauer, Fussgönheim, both of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/462,645

(22) PCT Filed: Jul. 2, 1998

(86) PCT No.: PCT/EP98/04097

§ 371 (c)(1),
(2), (4) Date: Jan. 11, 2000

(87) PCT Pub. No.: WO99/05285

PCT Pub. Date: Feb. 4, 1999

(30) Foreign Application Priority Data

Jul. 22, 1997 (DE) .......................... 197 31 274

(51) Int. Cl.$^7$ .......................... C12P 17/18; C12N 9/00; C12N 1/21; C12N 15/52; C07M 21/04
(52) U.S. Cl. .................... 435/119; 435/41; 435/183; 435/252.3; 435/254.11; 435/254.2; 435/320.1; 435/440; 536/23.2
(58) Field of Search .................. 435/183, 41, 320.1, 435/119, 252.3, 254.11, 254.2, 410

(56) References Cited

U.S. PATENT DOCUMENTS 6,361,978 B1    3/2002    Hoshino et al. ............ 435/119

FOREIGN PATENT DOCUMENTS

| EP | 0 236 429 B1 | 4/1993 |
| EP | 0 635 572 A2 | 6/1994 |
| EP | 0 449 721 B1 | 5/1997 |
| EP | 0 806 479 | 11/1997 |
| WO | WO 94/08023 | 4/1994 |

OTHER PUBLICATIONS

Brown et al., "The Production of Biotin by Genetically Modified Micro–Organisms", Biotechnology and Genetic Engineering Reviews, vol. 9, (12/91) pp. 295–326.

DeMoll, "Biosynthesis of Biotin and Lipoic Acid" (1996), pp. 704–709.

LeMoine et al., "To Be Free or not: the fate of pimelate in *Bacillus sphaericus* and in *Escherichia coli*", Molecular Microbiology, vol. 19 (1996), pp. 645–647.

Otsuka et al., "The *Escherichia coli* Biotin Biosynthetic Enzyme Sequences Predicted form the Nucleotide Sequence of the bio Operon", Journal of Biological Chemistry, vol. 263, No. 36 (1988), pp. 19577–19585.

Bower et al., "Cloning, Sequencing, and Characterization of the *Bacillus subtilis* Biotin Biosynthetic Operon", Journal of Bacteriology, vol. 178, No. 14, (7/96), pp. 4122–4130.

Kaneko et al., "Sequence Analysis of the Genome of the Unicellular Cyanobacterium *Synechocystis* sp. Strain PCC6803. II. Sequence Determination of the Entire Genome and Assignments of Potential Protein–coding Regions", DNA Research, vol. 3 (1996), pp. 109–136.

Zhang et al., The Gene for Biotin Synthase for *Saccharomyces cerevisiae:* Cloning, Sequencing, and Complementation of *Escherichia coli* Strains Lacking Biotin Synthase Archives of Biochemistry and Biophysics, vol. 309, No. 1, (2/94) pp. 29–35.

Baldet et al., "Biotin synthesis in higher plants: isolation of a cDNA encoding *Arabidopsis thaliana* BioB–gene product equivalent by functional complementation of a biotin auxotroph mutant bioB105 of *Escherichia coli* K12" C.R. Acad. Sci. Paris, Sciences de la ie/Life Sciences (1996) pp. 99–106.

PAI, C.H., "Mutant of *Escherichia coli* with Derepressed Levels of the Biotin Biosynthetic Enzymes" Journal of Bacteriology, vol. 112, No. 3(12/72) pp. 1280–1287.

Sanyal et al., "*Exchericia coli* Biotin Synthase: An Investigation into the Factors Required for Its Activity and Its Sulfur Donor", Archives of Biochemistry and Biophysics, vol. 326, No. 1 (2/96) pp. 48–56.

Sanyal et al., "Biotin Synthase: Purification, Characterization as a [2Fe–2S] Cluster Protein, and in Vitro Activity of the *Escherichia coli* bioB Gene Product", Biochemistry vol. 33, (1994) pp. 3625–3631.

Baldet et al., "Biotin biosynthesis in higher plant cells Identification of intermediates" European Journal of Biochemical vol. 217 (1993) pp. 479–485.

Mejean et al., "Highly Purified Biotin Synthase Can Transform Dethiobiotin Into Biotin In the Absence Of Any Other Protein, In the Presence Of Photoreduced Deazaflavin" Biochemical and Biophysical Research Communications, vol. 217, No. 3 (1995) pp. 1231–1237.

Ohshiro et al., "Enzymatic Conversion of Dethiobiotin to Biotin in Cell–free Extracts of a *Bacilus sphaericus* bioB Transformant", Biosci, Biotech, Biochem., vol. 58, No. 9 (1994) pp. 1738–1741.

Birch et al. "Biotin Synthase from *Escherichia coli*, an Investigation of the Low Molecular Weight and Protein Components Required for Activity in Vitro*", The Journal of Biological Chemistry, vol. 270, No. 32 (8/95) pp. 19158–19165.

(List continued on next page.)

Primary Examiner—Elizabeth Slobodyansky
(74) Attorney, Agent, or Firm—Keil & Weinkauf

(57) ABSTRACT

A gene construct comprising a biotin gene having the sequence SEQ ID No. 1 or SEQ ID No. 3, organisms which comprise this gene construct, the use of these sequences or of the gene construct for preparing biotin, and a process for preparing biotin are described.

7 Claims, 4 Drawing Sheets

OTHER PUBLICATIONS

Ifuku et al., "Molecular Analysis of Growth Inhibition Caused by Overexpression of the Biotin Operon in *Escherichia coli*", Biosci, Biotech, Biochem., vol. 59, No. 2 (1995), pp. 184–189.

Aiba et al., "A 580–kb DNA Sequence of the *Escherichia coli* K–12 Genome Corresponding to the 28.0–40.1 min Region on the Linkage Map", DNA Research vol. 3, (1996) pp. 363–377.

Zheng et al. "Cysteine desulfurase activity indicates a role for NIFS in metallocluster biosynthesis", Pro. Natl. Acad. Sci., USA, vol. 90, (4/93), pp. 2754–2758.

Zheng et al. "Mechanism for the Desulfurization of $_L$–Cysteine Catalyzed by the nifS Gene Product†", Biochemistry, vol. 33 (1994) pp. 4714–4720.

Fleischmann et al., "Whole–Genome Random Sequencing and Assembly of *Haemophilus influenzae* Rd" Science, vol. 269, (7/95) pp. 496–512.

Schroeder et al., "DnaK, DnaJ and GrpE form a cellular chaperone machinery capable of reparing heat–induced protein damage", The EMBO Journal, vol. 12, No. 11 (1993) pp. 4137–4144.

Zheng et al., "Catalytic Formation of a Nitrogenase Iron–Sulfur Cluster*" The Journal of Biological Chemistry, vol. 269, No. 29(1994) pp. 18723–18726.

Ifuku et al., "Flaodoxin is required for conversion of dethiobiotin to biotin in *Escherichia coli*" Eur. J. Biochem., vol. 224, (1994) pp. 173–178.

SEQUENCE LISTING

<160> NUMBER OF SEQ ID NOS: 38

<210> SEQ ID NO 1
<211> LENGTH: 1216
<212> TYPE: DNA
<213> ORGANISM: E. Coli w3110
<220> FEATURE:
<221> NAME/KEY: 5'UTR
<222> LOCATION: 1...11
<221> NAME/KEY: CDS
<222> LOCATION: 12...1216

<400> SEQUENCE: 1

```
cgaggagtac c atg aac gtt ttt aat ccc gcg cag ttt cgc gcc cag ttt      50
            Met Asn Val Phe Asn Pro Ala Gln Phe Arg Ala Gln Phe
             1               5                  10 ccc gca cta cag gat gcg ggc gtc tat ctc gac agc gcc gcg acc gcg      98
Pro Ala Leu Gln Asp Ala Gly Val Tyr Leu Asp Ser Ala Ala Thr Ala
      15                  20                  25 ctt aaa cct gaa gcc gtg gtt gaa gcc acc caa cag ttt tac agt ctg     146
Leu Lys Pro Glu Ala Val Val Glu Ala Thr Gln Gln Phe Tyr Ser Leu
 30                  35                  40                  45 agc gcc gga aac gtc cat cgc agc cag ttt gcc gaa gcc caa cgc ctg     194
Ser Ala Gly Asn Val His Arg Ser Gln Phe Ala Glu Ala Gln Arg Leu
                  50                  55                  60 acc gcg cgt tat gaa gct gca cga gag aaa gtg gcg caa tta ctg aat     242
Thr Ala Arg Tyr Glu Ala Ala Arg Glu Lys Val Ala Gln Leu Leu Asn
              65                  70                  75 gca ccg gat gat aaa act atc gtc tgg acg cgc ggc acc act gaa tcc     290
Ala Pro Asp Asp Lys Thr Ile Val Trp Thr Arg Gly Thr Thr Glu Ser
          80                  85                  90 atc aac atg gtg gca caa tgc tat gcg cgt ccg cgt ctg caa ccg ggc     338
Ile Asn Met Val Ala Gln Cys Tyr Ala Arg Pro Arg Leu Gln Pro Gly
```

-continued

|  |  |  |
|---|---|---|
|           95                       100                     105 | | |
| gat gag att att gtc agc gtg gca gaa cac cac gcc aac ctc gtc ccc<br>Asp Glu Ile Ile Val Ser Val Ala Glu His His Ala Asn Leu Val Pro<br>110                       115                     120                     125 | | 386 |
| tgg ctg atg gtc gcc caa caa act gga gcc aaa gtg gtg aaa ttg ccg<br>Trp Leu Met Val Ala Gln Gln Thr Gly Ala Lys Val Val Lys Leu Pro<br>                  130                     135                     140 | | 434 |
| ctt aat gcg cag cga ctg ccg gat gtc gat ttg ttg cca gaa ctg att<br>Leu Asn Ala Gln Arg Leu Pro Asp Val Asp Leu Leu Pro Glu Leu Ile<br>                  145                     150                     155 | | 482 |
| act ccc cgt agt cgg att ctg gcg ttg ggt cag atg tcg aac gtt act<br>Thr Pro Arg Ser Arg Ile Leu Ala Leu Gly Gln Met Ser Asn Val Thr<br>                      160                     165                     170 | | 530 |
| ggc ggt tgc ccg gat ctg gcg cga gcg att acc ttt gct cat tca gcc<br>Gly Gly Cys Pro Asp Leu Ala Arg Ala Ile Thr Phe Ala His Ser Ala<br>175                       180                     185 | | 578 |
| ggg atg gtg gtg atg gtt gat ggt gct cag ggg gca gtg cat ttc ccc<br>Gly Met Val Val Met Val Asp Gly Ala Gln Gly Ala Val His Phe Pro<br>190                       195                     200                     205 | | 626 |
| gcg gat gtt cag caa ctg gat att gat ttc tat gct ttt tca ggt cac<br>Ala Asp Val Gln Gln Leu Asp Ile Asp Phe Tyr Ala Phe Ser Gly His<br>                  210                     215                     220 | | 674 |
| aaa ctg tat ggc ccg aca ggt atc ggc gtg ctg tat ggt aaa tca gaa<br>Lys Leu Tyr Gly Pro Thr Gly Ile Gly Val Leu Tyr Gly Lys Ser Glu<br>                  225                     230                     235 | | 722 |
| ctg ctg gag gcg atg tcg ccc tgg ctg ggc ggc ggc aaa atg gtt cac<br>Leu Leu Glu Ala Met Ser Pro Trp Leu Gly Gly Gly Lys Met Val His<br>                  240                     245                     250 | | 770 |
| gaa gtg agt ttt gac ggc ttc acg act caa tct gcg ccg tgg aaa ctg<br>Glu Val Ser Phe Asp Gly Phe Thr Thr Gln Ser Ala Pro Trp Lys Leu<br>255                       260                     265 | | 818 |
| gaa gct gga acg cca aat gtc gct ggt gtc ata gga tta agc gcg gcg<br>Glu Ala Gly Thr Pro Asn Val Ala Gly Val Ile Gly Leu Ser Ala Ala<br>270                       275                     280                     285 | | 866 |
| ctg gaa tgg ctg gca gat tac gat atc aac cag gcc gaa agc tgg agc<br>Leu Glu Trp Leu Ala Asp Tyr Asp Ile Asn Gln Ala Glu Ser Trp Ser<br>                  290                     295                     300 | | 914 |
| cgt agc tta gca acg ctg gcg gaa gat gcg ctg gcg aaa cgt ccc ggc<br>Arg Ser Leu Ala Thr Leu Ala Glu Asp Ala Leu Ala Lys Arg Pro Gly<br>                  305                     310                     315 | | 962 |
| ttt cgt tca ttc cgc tgc cag gat tcc agc ctg ctg gcc ttt gat ttt<br>Phe Arg Ser Phe Arg Cys Gln Asp Ser Ser Leu Leu Ala Phe Asp Phe<br>                  320                     325                     330 | | 1010 |
| gct ggc gtt cat cat agc gat atg gtg acg ctg ctg gcg gag tac ggt<br>Ala Gly Val His His Ser Asp Met Val Thr Leu Leu Ala Glu Tyr Gly<br>335                       340                     345 | | 1058 |
| att gcc ctg cgg gcc ggg cag cat tgc gct cag ccg cta ctg gca gaa<br>Ile Ala Leu Arg Ala Gly Gln His Cys Ala Gln Pro Leu Leu Ala Glu<br>350                       355                     360                     365 | | 1106 |
| tta ggc gta acc ggc aca ctg cgc gcc tct ttt gcg cca tat aat aca<br>Leu Gly Val Thr Gly Thr Leu Arg Ala Ser Phe Ala Pro Tyr Asn Thr<br>                  370                     375                     380 | | 1154 |
| aag agt gat gtg gat gcg ctg gtg aat gcc gtt gac cgc gcg ctg gaa<br>Lys Ser Asp Val Asp Ala Leu Val Asn Ala Val Asp Arg Ala Leu Glu<br>                  385                     390                     395 | | 1202 |
| tta ttg gtg gat ta<br>Leu Leu Val Asp<br>             400 | | 1216 |

```
<210> SEQ ID NO 2
<211> LENGTH: 401
<212> TYPE: PRT
<213> ORGANISM: E. Coli w3110

<400> SEQUENCE: 2

Met Asn Val Phe Asn Pro Ala Gln Phe Arg Ala Gln Phe Pro Ala Leu
 1               5                  10                  15

Gln Asp Ala Gly Val Tyr Leu Asp Ser Ala Ala Thr Ala Leu Lys Pro
            20                  25                  30

Glu Ala Val Val Glu Ala Thr Gln Gln Phe Tyr Ser Leu Ser Ala Gly
        35                  40                  45

Asn Val His Arg Ser Gln Phe Ala Glu Ala Gln Arg Leu Thr Ala Arg
    50                  55                  60

Tyr Glu Ala Ala Arg Glu Lys Val Ala Gln Leu Leu Asn Ala Pro Asp
 65                  70                  75                  80

Asp Lys Thr Ile Val Trp Thr Arg Gly Thr Thr Glu Ser Ile Asn Met
                85                  90                  95

Val Ala Gln Cys Tyr Ala Arg Pro Arg Leu Gln Pro Gly Asp Glu Ile
            100                 105                 110

Ile Val Ser Val Ala Glu His His Ala Asn Leu Val Pro Trp Leu Met
        115                 120                 125

Val Ala Gln Gln Thr Gly Ala Lys Val Val Lys Leu Pro Leu Asn Ala
    130                 135                 140

Gln Arg Leu Pro Asp Val Asp Leu Leu Pro Glu Leu Ile Thr Pro Arg
145                 150                 155                 160

Ser Arg Ile Leu Ala Leu Gly Gln Met Ser Asn Val Thr Gly Gly Cys
                165                 170                 175

Pro Asp Leu Ala Arg Ala Ile Thr Phe Ala His Ser Ala Gly Met Val
            180                 185                 190

Val Met Val Asp Gly Ala Gln Gly Ala Val His Phe Pro Ala Asp Val
        195                 200                 205

Gln Gln Leu Asp Ile Asp Phe Tyr Ala Phe Ser Gly His Lys Leu Tyr
    210                 215                 220

Gly Pro Thr Gly Ile Gly Val Leu Tyr Gly Lys Ser Glu Leu Leu Glu
225                 230                 235                 240

Ala Met Ser Pro Trp Leu Gly Gly Gly Lys Met Val His Glu Val Ser
                245                 250                 255

Phe Asp Gly Phe Thr Thr Gln Ser Ala Pro Trp Lys Leu Glu Ala Gly
            260                 265                 270

Thr Pro Asn Val Ala Gly Val Ile Gly Leu Ser Ala Ala Leu Glu Trp
        275                 280                 285

Leu Ala Asp Tyr Asp Ile Asn Gln Ala Glu Ser Trp Ser Arg Ser Leu
    290                 295                 300

Ala Thr Leu Ala Glu Asp Ala Leu Ala Lys Arg Pro Gly Phe Arg Ser
305                 310                 315                 320

Phe Arg Cys Gln Asp Ser Ser Leu Leu Ala Phe Asp Phe Ala Gly Val
                325                 330                 335

His His Ser Asp Met Val Thr Leu Leu Ala Glu Tyr Gly Ile Ala Leu
            340                 345                 350

Arg Ala Gly Gln His Cys Ala Gln Pro Leu Leu Ala Glu Leu Gly Val
        355                 360                 365

Thr Gly Thr Leu Arg Ala Ser Phe Ala Pro Tyr Asn Thr Lys Ser Asp
    370                 375                 380
```

```
Val Asp Ala Leu Val Asn Ala Val Asp Arg Ala Leu Glu Leu Leu Val
385                 390                 395                 400

Asp

<210> SEQ ID NO 3
<211> LENGTH: 1232
<212> TYPE: DNA
<213> ORGANISM: E. Coli w3110
<220> FEATURE:
<221> NAME/KEY: 5'UTR
<222> LOCATION: 1...18
<221> NAME/KEY: CDS
<222> LOCATION: 19...1232

<400> SEQUENCE: 3
aaagaggaga aattaact atg aaa tta ccg att tat ctc gac tac tcc gca         51
                   Met Lys Leu Pro Ile Tyr Leu Asp Tyr Ser Ala
                    1               5                  10 acc acg ccg gtg gac ccg cgt gtt gcc gag aaa atg atg cag ttt atg        99
Thr Thr Pro Val Asp Pro Arg Val Ala Glu Lys Met Met Gln Phe Met
            15                  20                  25 acg atg gac gga acc ttt ggt aac ccg gcc tcc cgt tct cac cgt ttc       147
Thr Met Asp Gly Thr Phe Gly Asn Pro Ala Ser Arg Ser His Arg Phe
        30                  35                  40 ggc tgg cag gct gaa gaa gcg gta gat atc gcc cgt aat cag att gcc       195
Gly Trp Gln Ala Glu Glu Ala Val Asp Ile Ala Arg Asn Gln Ile Ala
    45                  50                  55 gat ctg gtc ggc gct gat ccg cgt gaa atc gtc ttt acc tct ggt gca       243
Asp Leu Val Gly Ala Asp Pro Arg Glu Ile Val Phe Thr Ser Gly Ala
60                  65                  70                  75 acc gaa tct gac aac ctg gcg atc aaa ggt gca gcc aac ttt tat cag       291
Thr Glu Ser Asp Asn Leu Ala Ile Lys Gly Ala Ala Asn Phe Tyr Gln
                80                  85                  90 aaa aaa ggc aag cac atc atc acc agc aaa acc gaa cac aaa gcg gta       339
Lys Lys Gly Lys His Ile Ile Thr Ser Lys Thr Glu His Lys Ala Val
            95                 100                 105 ctg gat acc tgc cgt cag ctg gag cgc gaa ggt ttt gaa gtc acc tac       387
Leu Asp Thr Cys Arg Gln Leu Glu Arg Glu Gly Phe Glu Val Thr Tyr
        110                 115                 120 ctg gca ccg cag cgt aac ggc att atc gac ctg aaa gaa ctt gaa gca       435
Leu Ala Pro Gln Arg Asn Gly Ile Ile Asp Leu Lys Glu Leu Glu Ala
    125                 130                 135 gcg atg cgt gac gac acc atc ctc gtg tcc atc atg cac gta aat aac       483
Ala Met Arg Asp Asp Thr Ile Leu Val Ser Ile Met His Val Asn Asn
140                 145                 150                 155 gaa atc ggc gtg gtg cag gat atc gcg gct atc ggc gaa atg tgc cgt       531
Glu Ile Gly Val Val Gln Asp Ile Ala Ala Ile Gly Glu Met Cys Arg
                160                 165                 170 gct cgt ggc att atc tat cac gtt gat gca acc cag agc gtg ggt aaa       579
Ala Arg Gly Ile Ile Tyr His Val Asp Ala Thr Gln Ser Val Gly Lys
            175                 180                 185 ctg cct atc gac ctg agc cag ttg aaa gtt gac ctg atg tct ttc tcc       627
Leu Pro Ile Asp Leu Ser Gln Leu Lys Val Asp Leu Met Ser Phe Ser
        190                 195                 200 ggt cac aaa atc tat ggc ccg aaa ggt atc ggt gcg ctg tat gta cgt       675
Gly His Lys Ile Tyr Gly Pro Lys Gly Ile Gly Ala Leu Tyr Val Arg
    205                 210                 215 cgt aaa ccg cgc gta cgc atc gaa gcg caa atg cac ggc ggt ggt cac       723
Arg Lys Pro Arg Val Arg Ile Glu Ala Gln Met His Gly Gly Gly His
220                 225                 230                 235 gag cgc ggt atg cgt tcc ggc act ctg cct gtt cac cag atc gtc gga       771
```

```
                 Glu Arg Gly Met Arg Ser Gly Thr Leu Pro Val His Gln Ile Val Gly
                                 240                 245                 250 atg ggc gag gcc tat cgc atc gca aaa gaa gag atg gcg acc gag atg                    819
Met Gly Glu Ala Tyr Arg Ile Ala Lys Glu Glu Met Ala Thr Glu Met
            255                 260                 265 gaa cgt ctg cgc ggc ctg cgt aac cgt ctg tgg aac ggc atc aaa gat                    867
Glu Arg Leu Arg Gly Leu Arg Asn Arg Leu Trp Asn Gly Ile Lys Asp
270                 275                 280 atc gaa gaa gtt tac ctg aac ggt gac ctg gaa cac ggt gcg ccg aac                    915
Ile Glu Glu Val Tyr Leu Asn Gly Asp Leu Glu His Gly Ala Pro Asn
        285                 290                 295 att ctc aac gtc agc ttc aac tac gtt gaa ggt gag tcg ctg att atg                    963
Ile Leu Asn Val Ser Phe Asn Tyr Val Glu Gly Glu Ser Leu Ile Met
300                 305                 310                 315 gcg ctg aaa gac ctc gca gtt tct tca ggt tcc gcc tgt acg tca gca                   1011
Ala Leu Lys Asp Leu Ala Val Ser Ser Gly Ser Ala Cys Thr Ser Ala
            320                 325                 330 agc ctc gaa ccg tcc tac gtg ctg cgc gcg ctg ggg ctg aac gac gag                   1059
Ser Leu Glu Pro Ser Tyr Val Leu Arg Ala Leu Gly Leu Asn Asp Glu
                335                 340                 345 ctg gca cat agc tct atc cgt ttc tct tta ggt cgt ttt act act gaa                   1107
Leu Ala His Ser Ser Ile Arg Phe Ser Leu Gly Arg Phe Thr Thr Glu
        350                 355                 360 gaa gag atc gac tac acc atc gag tta gtt cgt aaa tcc atc ggt cgt                   1155
Glu Glu Ile Asp Tyr Thr Ile Glu Leu Val Arg Lys Ser Ile Gly Arg
365                 370                 375 ctg cgt gac ctt tct ccg ctg tgg gaa atg tac aag cag ggc gtg gat                   1203
Leu Arg Asp Leu Ser Pro Leu Trp Glu Met Tyr Lys Gln Gly Val Asp
380                 385                 390                 395 ctg aac agc atc gaa tgg gct cat cat ta                                            1232
Leu Asn Ser Ile Glu Trp Ala His His
                400

<210> SEQ ID NO 4
<211> LENGTH: 404
<212> TYPE: PRT
<213> ORGANISM: E. Coli w3110

<400> SEQUENCE: 4

Met Lys Leu Pro Ile Tyr Leu Asp Tyr Ser Ala Thr Thr Pro Val Asp
 1               5                  10                  15

Pro Arg Val Ala Glu Lys Met Met Gln Phe Met Thr Met Asp Gly Thr
             20                  25                  30

Phe Gly Asn Pro Ala Ser Arg Ser His Arg Phe Gly Trp Gln Ala Glu
         35                  40                  45

Glu Ala Val Asp Ile Ala Arg Asn Gln Ile Ala Asp Leu Val Gly Ala
     50                  55                  60

Asp Pro Arg Glu Ile Val Phe Thr Ser Gly Ala Thr Glu Ser Asp Asn
 65                  70                  75                  80

Leu Ala Ile Lys Gly Ala Ala Asn Phe Tyr Gln Lys Lys Gly Lys His
                 85                  90                  95

Ile Ile Thr Ser Lys Thr Glu His Lys Ala Val Leu Asp Thr Cys Arg
            100                 105                 110

Gln Leu Glu Arg Glu Gly Phe Glu Val Thr Tyr Leu Ala Pro Gln Arg
        115                 120                 125

Asn Gly Ile Ile Asp Leu Lys Glu Leu Glu Ala Ala Met Arg Asp Asp
    130                 135                 140

Thr Ile Leu Val Ser Ile Met His Val Asn Asn Glu Ile Gly Val Val
```

```
                145                 150                 155                 160

Gln Asp Ile Ala Ala Ile Gly Glu Met Cys Arg Ala Arg Gly Ile Ile
                165                 170                 175

Tyr His Val Asp Ala Thr Gln Ser Val Gly Lys Leu Pro Ile Asp Leu
            180                 185                 190

Ser Gln Leu Lys Val Asp Leu Met Ser Phe Ser Gly His Lys Ile Tyr
        195                 200                 205

Gly Pro Lys Gly Ile Gly Ala Leu Tyr Val Arg Arg Lys Pro Arg Val
    210                 215                 220

Arg Ile Glu Ala Gln Met His Gly Gly His Glu Arg Gly Met Arg
225                 230                 235                 240

Ser Gly Thr Leu Pro Val His Gln Ile Val Gly Met Gly Glu Ala Tyr
                245                 250                 255

Arg Ile Ala Lys Glu Glu Met Ala Thr Glu Met Glu Arg Leu Arg Gly
                260                 265                 270

Leu Arg Asn Arg Leu Trp Asn Gly Ile Lys Asp Ile Glu Glu Val Tyr
            275                 280                 285

Leu Asn Gly Asp Leu Glu His Gly Ala Pro Asn Ile Leu Asn Val Ser
        290                 295                 300

Phe Asn Tyr Val Glu Gly Glu Ser Leu Ile Met Ala Leu Lys Asp Leu
305                 310                 315                 320

Ala Val Ser Ser Gly Ser Ala Cys Thr Ser Ala Ser Leu Glu Pro Ser
                325                 330                 335

Tyr Val Leu Arg Ala Leu Gly Leu Asn Asp Glu Leu Ala His Ser Ser
                340                 345                 350

Ile Arg Phe Ser Leu Gly Arg Phe Thr Thr Glu Glu Ile Asp Tyr
            355                 360                 365

Thr Ile Glu Leu Val Arg Lys Ser Ile Gly Arg Leu Arg Asp Leu Ser
        370                 375                 380

Pro Leu Trp Glu Met Tyr Lys Gln Gly Val Asp Leu Asn Ser Ile Glu
385                 390                 395                 400

Trp Ala His His

<210> SEQ ID NO 5
<211> LENGTH: 3794
<212> TYPE: DNA
<213> ORGANISM: clone pHS1bioS1
<220> FEATURE:
<221> NAME/KEY: CDS
<222> LOCATION: 601...1806

<400> SEQUENCE: 5
gacgtctgtg tggaattgtg agcggataac aatttcacac agggccctcg dacaccgagg      60
agaatgtcaa gaggcgaaca cacaacgtct tggagcgcca gaggaggaac gagctaaaac     120
ggagcttttt tgccctgcgt gaccagatcc cggagttgga aaacaatgaa aaggcccccca    180 aggtagttat ccttaaaaaa gccacagcat acatcctgtc cgtccaagca gaggagcaaa     240
agctcatttc tgaagaggac ttgttgcgga acgacgaga acagttgaaa cacaaacttg      300
aacagctacg gaactcttgt gcgtaaggaa agtaaggaa aacgattcct tctaacagaa      360
atgtcctgag caatcaccta tgaactgtcg actcgagata gcatttttat ccataagatt     420
agccgatcct aaggtttaca attgtgagcg ctcacaatta tgatagattc aattgtgagc     480
ggataacaat ttcacacacg ctagcggtac cgggcccccc ctcgaggtcg acggtatcga     540
taagcttgat atcgaattcc tgcagcccgg gggatcccat ggtacgcgtc gaggagtacc     600
```

| | | |
|---|---|---|
| atg aac gtt ttt aat ccc gcg cag ttt cgc gcc cag ttt ccc gca cta<br>Met Asn Val Phe Asn Pro Ala Gln Phe Arg Ala Gln Phe Pro Ala Leu<br>1                    5                      10                    15 | 648 |
| cag gat gcg ggc gtc tat ctc gac agc gcc gcg acc gcg ctt aaa cct<br>Gln Asp Ala Gly Val Tyr Leu Asp Ser Ala Ala Thr Ala Leu Lys Pro<br>                    20                      25                      30 | 696 |
| gaa gcc gtg gtt gaa gcc acc caa cag ttt tac agt ctg agc gcc gga<br>Glu Ala Val Val Glu Ala Thr Gln Gln Phe Tyr Ser Leu Ser Ala Gly<br>            35                      40                      45 | 744 |
| aac gtc cat cgc agc cag ttt gcc gaa gcc caa cgc ctg acc gcg cgt<br>Asn Val His Arg Ser Gln Phe Ala Glu Ala Gln Arg Leu Thr Ala Arg<br>    50                      55                      60 | 792 |
| tat gaa gct gca cga gag aaa gtg gcg caa tta ctg aat gca ccg gat<br>Tyr Glu Ala Ala Arg Glu Lys Val Ala Gln Leu Leu Asn Ala Pro Asp<br>65                    70                      75                    80 | 840 |
| gat aaa act atc gtc tgg acg cgc ggc acc act gaa tcc atc aac atg<br>Asp Lys Thr Ile Val Trp Thr Arg Gly Thr Thr Glu Ser Ile Asn Met<br>                      85                      90                    95 | 888 |
| gtg gca caa tgc tat gcg cgt ccg cgt ctg caa ccg ggc gat gag att<br>Val Ala Gln Cys Tyr Ala Arg Pro Arg Leu Gln Pro Gly Asp Glu Ile<br>          100                      105                      110 | 936 |
| att gtc agc gtg gca gaa cac cac gcc aac ctc gtc ccc tgg ctg atg<br>Ile Val Ser Val Ala Glu His His Ala Asn Leu Val Pro Trp Leu Met<br>          115                      120                      125 | 984 |
| gtc gcc caa caa act gga gcc aaa gtg gtg aaa ttg ccg ctt aat gcg<br>Val Ala Gln Gln Thr Gly Ala Lys Val Val Lys Leu Pro Leu Asn Ala<br>130                    135                      140 | 1032 |
| cag cga ctg ccg gat gtc gat ttg ttg cca gaa ctg att act ccc cgt<br>Gln Arg Leu Pro Asp Val Asp Leu Leu Pro Glu Leu Ile Thr Pro Arg<br>145                    150                      155                    160 | 1080 |
| agt cgg att ctg gcg ttg ggt cag atg tcg aac gtt act ggc ggt tgc<br>Ser Arg Ile Leu Ala Leu Gly Gln Met Ser Asn Val Thr Gly Gly Cys<br>                    165                      170                    175 | 1128 |
| ccg gat ctg gcg cga gcg att acc ttt gct cat tca gcc ggg atg gtg<br>Pro Asp Leu Ala Arg Ala Ile Thr Phe Ala His Ser Ala Gly Met Val<br>          180                      185                      190 | 1176 |
| gtg atg gtt gat ggt gct cag ggg gca gtg cat ttc ccc gcg gat gtt<br>Val Met Val Asp Gly Ala Gln Gly Ala Val His Phe Pro Ala Asp Val<br>          195                      200                      205 | 1224 |
| cag caa ctg gat att gat ttc tat gct ttt tca ggt cac aaa ctg tat<br>Gln Gln Leu Asp Ile Asp Phe Tyr Ala Phe Ser Gly His Lys Leu Tyr<br>210                    215                      220 | 1272 |
| ggc ccg aca ggt atc ggc gtg ctg tat ggt aaa tca gaa ctg ctg gag<br>Gly Pro Thr Gly Ile Gly Val Leu Tyr Gly Lys Ser Glu Leu Leu Glu<br>225                    230                      235                    240 | 1320 |
| gcg atg tcg ccc tgg ctg ggc ggc ggc aaa atg gtt cac gaa gtg agt<br>Ala Met Ser Pro Trp Leu Gly Gly Gly Lys Met Val His Glu Val Ser<br>                    245                      250                    255 | 1368 |
| ttt gac ggc ttc acg act caa tct gcg ccg tgg aaa ctg gaa gct gga<br>Phe Asp Gly Phe Thr Thr Gln Ser Ala Pro Trp Lys Leu Glu Ala Gly<br>          260                      265                      270 | 1416 |
| acg cca aat gtc gct ggt gtc ata gga tta agc gcg gcg ctg gaa tgg<br>Thr Pro Asn Val Ala Gly Val Ile Gly Leu Ser Ala Ala Leu Glu Trp<br>275                    280                      285 | 1464 |
| ctg gca gat tac gat atc aac cag gcc gaa agc tgg agc cgt agc tta<br>Leu Ala Asp Tyr Asp Ile Asn Gln Ala Glu Ser Trp Ser Arg Ser Leu<br>          290                      295                      300 | 1512 |
| gca acg ctg gcg gaa gat gcg ctg gcg aaa cgt ccc ggc ttt cgt tca<br>Ala Thr Leu Ala Glu Asp Ala Leu Ala Lys Arg Pro Gly Phe Arg Ser | 1560 |

```
                                                          -continued 305                  310                 315                 320 ttc cgc tgc cag gat tcc agc ctg ctg gcc ttt gat ttt gct ggc gtt     1608
Phe Arg Cys Gln Asp Ser Ser Leu Leu Ala Phe Asp Phe Ala Gly Val
                        325                 330                 335 cat cat agc gat atg gtg acg ctg ctg gcg gag tac ggt att gcc ctg     1656
His His Ser Asp Met Val Thr Leu Leu Ala Glu Tyr Gly Ile Ala Leu
                340                 345                 350 cgg gcc ggg cag cat tgc gct cag ccg cta ctg gca gaa tta ggc gta     1704
Arg Ala Gly Gln His Cys Ala Gln Pro Leu Leu Ala Glu Leu Gly Val
            355                 360                 365 acc ggc aca ctg cgc gcc tct ttt gcg cca tat aat aca aag agt gat     1752
Thr Gly Thr Leu Arg Ala Ser Phe Ala Pro Tyr Asn Thr Lys Ser Asp
        370                 375                 380 gtg gat gcg ctg gtg aat gcc gtt gac cgc gcg ctg gaa tta ttg gtg     1800
Val Asp Ala Leu Val Asn Ala Val Asp Arg Ala Leu Glu Leu Leu Val
385                 390                 395                 400 gat                                                                  1853
Asp
    taaacgcgtg ctagaggcat caaataaaac gaaaggctca gtcgaaagac tgggccttc gttttatctg ttgtttgtcg gtgaacgctc tcctgagtag acaaatccg     1913
ccgccctaga cctaggggat atattccgct tcctcgctca ctgactcgct acgctcggtc    1973
gttcgactgc ggcgagcgga aatggcttac gaacggggcg gagatttcct ggaagatgcc    2033
aggaagatac ttaacaggga agtgagaggg ccgcggcaaa gccgttttc cataggctcc     2093
gccccctga caagcatcac gaaatctgac gctcaaatca gtggtggcga acccgacag     2153
gactataaag ataccaggcg tttccccctg gcggctccct cgtgcgctct cctgttcctg    2213
cctttcggtt taccggtgtc attccgctgt tatggccgcg tttgtctcat tccacgcctg    2273
acactcagtt ccgggtaggc agttcgctcc aagctggact gtatgcacga acccccgtt    2333
cagtccgacc gctgcgcctt atccggtaac tatcgtcttg agtccaaccc ggaaagacat    2393
gcaaaagcac cactggcagc agccactggt aattgattta gaggagttag tcttgaagtc    2453
atgcgccggt taaggctaaa ctgaaaggac aagttttggt gactgcgctc ctccaagcca    2513
gttacctcgg ttcaaagagt tggtagctca gagaaccttc gaaaaccgc cctgcaaggc     2573
ggttttttcg ttttcagagc aagagattac gcgcagacca aaacgatctc aagaagatca    2633
tcttattaat cagataaaat atttctagat ttcagtgcaa tttatctctt caaatgtagc    2693
acctgaagtc agccccatac gatataagtt gttactagtg cttggattct caccaataaa    2753
aaacgcccgg cggcaaccga gcgttctgaa caaatccaga tggagttctg aggtcattac    2813
tggatctatc aacaggagtc caagcgagct ctcgaacccc agagtcccgc tcagaagaac    2873
tcgtcaagaa ggcgatagaa ggcgatgcgc tgcgaatcgg gagcggcgat accgtaaagc    2933
acgaggaagc ggtcagccca ttcgccgcca agctcttcag caatatcacg ggtagccaac    2993
gctatgtcct gatagcggtc cgccacaccc agccggccac agtcgatgaa tccagaaaag    3053
cggccatttt ccaccatgat attcggcaag caggcatcgc catgggtcac gacgagatcc    3113
tcgccgtcgg catgcgcgc cttgagcctg gcgaacagtt cggctggcgc gagcccctga    3173
tgctcttcgt ccagatcatc ctgatcgaca agaccggctt ccatccgagt acgtgctcgc    3233
tcgatgcgat gtttcgcttg gtggtcgaat gggcaggtag ccggatcaag cgtatgcagc    3293
cgccgcattg catcagccat gatggatact ttctcggcag gagcaaggtg agatgacagg    3353
agatcctgcc ccggcacttc gcccaatagc agccagtccc ttcccgcttc agtgacaacg    3413
tcgagcacag ctgcgcaagg aacgcccgtc gtggccagcc acgatagccg cgctgcctcg    3473
```

-continued

```
tcctgcagtt cattcagggc accggacagg tcggtcttga caaaaagaac cgggcgcccc    3533
tgcgctgaca gccggaacac ggcggcatca gagcagccga ttgtctgttg tgcccagtca    3593
tagccgaata gcctctccac ccaagcggcc ggagaacctg cgtgcaatcc atcttgttca    3653
atcatgcgaa acgatcctca tcctgtctct tgatcagatc ttgatcccct gcgccatcag    3713
atccttggcg gcaagaaagc catccagttt actttgcagg gcttcccaac cttaccagag    3773
ggcgccccag ctggcaattc c                                              3794
```

<210> SEQ ID NO 6
<211> LENGTH: 401
<212> TYPE: PRT
<213> ORGANISM: clone pHS1bioS1

<400> SEQUENCE: 6

| | | | | | | | | | | | | | | |
|---|---|---|---|---|---|---|---|---|---|---|---|---|---|---|
| Met | Asn | Val | Phe | Asn | Pro | Ala | Gln | Phe | Arg | Ala | Gln | Phe | Pro | Ala | Leu |
| 1 | | | | 5 | | | | | 10 | | | | | 15 | |

Gln Asp Ala Gly Val Tyr Leu Asp Ser Ala Ala Thr Ala Leu Lys Pro
            20                  25                  30

Glu Ala Val Val Glu Ala Thr Gln Gln Phe Tyr Ser Leu Ser Ala Gly
        35                  40                  45

Asn Val His Arg Ser Gln Phe Ala Glu Ala Gln Arg Leu Thr Ala Arg
    50                  55                  60

Tyr Glu Ala Ala Arg Glu Lys Val Ala Gln Leu Leu Asn Ala Pro Asp
65                  70                  75                  80

Asp Lys Thr Ile Val Trp Thr Arg Gly Thr Thr Glu Ser Ile Asn Met
                85                  90                  95

Val Ala Gln Cys Tyr Ala Arg Pro Arg Leu Gln Pro Gly Asp Glu Ile
            100                 105                 110

Ile Val Ser Val Ala Glu His His Ala Asn Leu Val Pro Trp Leu Met
        115                 120                 125

Val Ala Gln Gln Thr Gly Ala Lys Val Val Lys Leu Pro Leu Asn Ala
    130                 135                 140

Gln Arg Leu Pro Asp Val Asp Leu Leu Pro Glu Leu Ile Thr Pro Arg
145                 150                 155                 160

Ser Arg Ile Leu Ala Leu Gly Gln Met Ser Asn Val Thr Gly Gly Cys
                165                 170                 175

Pro Asp Leu Ala Arg Ala Ile Thr Phe Ala His Ser Ala Gly Met Val
            180                 185                 190

Val Met Val Asp Gly Ala Gln Gly Ala Val His Phe Pro Ala Asp Val
        195                 200                 205

Gln Gln Leu Asp Ile Asp Phe Tyr Ala Phe Ser Gly His Lys Leu Tyr
    210                 215                 220

Gly Pro Thr Gly Ile Gly Val Leu Tyr Gly Lys Ser Glu Leu Leu Glu
225                 230                 235                 240

Ala Met Ser Pro Trp Leu Gly Gly Lys Met Val His Glu Val Ser
                245                 250                 255

Phe Asp Gly Phe Thr Thr Gln Ser Ala Pro Trp Lys Leu Glu Ala Gly
            260                 265                 270

Thr Pro Asn Val Ala Gly Val Ile Gly Leu Ser Ala Ala Leu Glu Trp
        275                 280                 285

Leu Ala Asp Tyr Asp Ile Asn Gln Ala Glu Ser Trp Ser Arg Ser Leu
    290                 295                 300

Ala Thr Leu Ala Glu Asp Ala Leu Ala Lys Arg Pro Gly Phe Arg Ser
305                 310                 315                 320

-continued

```
Phe Arg Cys Gln Asp Ser Ser Leu Leu Ala Phe Asp Phe Ala Gly Val
            325                 330                 335

His His Ser Asp Met Val Thr Leu Leu Ala Glu Tyr Gly Ile Ala Leu
        340                 345                 350

Arg Ala Gly Gln His Cys Ala Gln Pro Leu Leu Ala Glu Leu Gly Val
            355                 360                 365

Thr Gly Thr Leu Arg Ala Ser Phe Ala Pro Tyr Asn Thr Lys Ser Asp
        370                 375                 380

Val Asp Ala Leu Val Asn Ala Val Asp Arg Ala Leu Glu Leu Leu Val
385                 390                 395                 400

Asp

<210> SEQ ID NO 7
<211> LENGTH: 3810
<212> TYPE: DNA
<213> ORGANISM: clone pHS1bioS2
<220> FEATURE:
<221> NAME/KEY: CDS
<222> LOCATION: 608...1822

<400> SEQUENCE: 7
gacgtctgtg tggaattgtg agcggataac aatttcacac agggccctcg gacaccgagg      60
agaatgtcaa gaggcgaaca cacaacgtct tggagcgcca gaggaggaac gagctaaaac     120 ggagctttt tgccctgcgt gaccagatcc cggagttgga aaacaatgaa aaggccccca     180
aggtagttat ccttaaaaaa gccacagcat acatcctgtc cgtccaagca gaggagcaaa     240
agctcatttc tgaagaggac ttgttgcgga acgacgaga acagttgaaa cacaaacttg     300
aacagctacg gaactcttgt gcgtaaggaa aagtaaggaa aacgattcct tctaacagaa     360
atgtcctgag caatcaccta tgaactgtcg actcgagata gcatttttat ccataagatt     420
agccgatcct aaggtttaca attgtgagcg ctcacaatta tgatagattc aattgtgagc     480
ggataacaat ttcacacacg ctagcggtac cgggcccccc ctcgaggtcg acggtatcga     540
taagcttgat atcgaattcc tgcagcccgg gggatcccat ggtacgcgta agaggagaa     600 attaact atg aaa tta ccg att tat ctc gac tac tcc gca acc acg ccg       649
        Met Lys Leu Pro Ile Tyr Leu Asp Tyr Ser Ala Thr Thr Pro
        1               5                   10 gtg gac ccg cgt gtt gcc gag aaa atg atg cag ttt atg acg atg gac       697
Val Asp Pro Arg Val Ala Glu Lys Met Met Gln Phe Met Thr Met Asp
15                  20                  25                  30 gga acc ttt ggt aac ccg gcc tcc cgt tct cac cgt ttc ggc tgg cag       745
Gly Thr Phe Gly Asn Pro Ala Ser Arg Ser His Arg Phe Gly Trp Gln
                35                  40                  45 gct gaa gaa gcg gta gat atc gcc cgt aat cag att gcc gat ctg gtc       793
Ala Glu Glu Ala Val Asp Ile Ala Arg Asn Gln Ile Ala Asp Leu Val
            50                  55                  60 ggc gct gat ccg cgt gaa atc gtc ttt acc tct ggt gca acc gaa tct       841
Gly Ala Asp Pro Arg Glu Ile Val Phe Thr Ser Gly Ala Thr Glu Ser
        65                  70                  75 gac aac ctg gcg atc aaa ggt gca gcc aac ttt tat cag aaa aaa ggc       889
Asp Asn Leu Ala Ile Lys Gly Ala Ala Asn Phe Tyr Gln Lys Lys Gly
    80                  85                  90 aag cac atc atc acc agc aaa acc gaa cac aaa gcg gta ctg gat acc       937
Lys His Ile Ile Thr Ser Lys Thr Glu His Lys Ala Val Leu Asp Thr
95                  100                 105                 110 tgc cgt cag ctg gag cgc gaa ggt ttt gaa gtc acc tac ctg gca ccg       985
Cys Arg Gln Leu Glu Arg Glu Gly Phe Glu Val Thr Tyr Leu Ala Pro
```

-continued

```
              115                 120                      125
cag cgt aac ggc att atc gac ctg aaa gaa ctt gaa gca gcg atg cgt    1033
Gln Arg Asn Gly Ile Ile Asp Leu Lys Glu Leu Glu Ala Ala Met Arg
            130                 135                 140 gac gac acc atc ctc gtg tcc atc atg cac gta aat aac gaa atc ggc    1081
Asp Asp Thr Ile Leu Val Ser Ile Met His Val Asn Asn Glu Ile Gly
        145                 150                 155 gtg gtg cag gat atc gcg gct atc ggc gaa atg tgc cgt gct cgt ggc    1129
Val Val Gln Asp Ile Ala Ala Ile Gly Glu Met Cys Arg Ala Arg Gly
    160                 165                 170 att atc tat cac gtt gat gca acc cag agc gtg ggt aaa ctg cct atc    1177
Ile Ile Tyr His Val Asp Ala Thr Gln Ser Val Gly Lys Leu Pro Ile
175                 180                 185                 190 gac ctg agc cag ttg aaa gtt gac ctg atg tct ttc tcc ggt cac aaa    1225
Asp Leu Ser Gln Leu Lys Val Asp Leu Met Ser Phe Ser Gly His Lys
                195                 200                 205 atc tat ggc ccg aaa ggt atc ggt gcg ctg tat gta cgt cgt aaa ccg    1273
Ile Tyr Gly Pro Lys Gly Ile Gly Ala Leu Tyr Val Arg Arg Lys Pro
            210                 215                 220 cgc gta cgc atc gaa gcg caa atg cac ggc ggt cac gag cgc ggt        1321
Arg Val Arg Ile Glu Ala Gln Met His Gly Gly His Glu Arg Gly
        225                 230                 235 atg cgt tcc ggc act ctg cct gtt cac cag atc gtc gga atg ggc gag    1369
Met Arg Ser Gly Thr Leu Pro Val His Gln Ile Val Gly Met Gly Glu
    240                 245                 250 gcc tat cgc atc gca aaa gaa gag atg gcg acc gag atg gaa cgt ctg    1417
Ala Tyr Arg Ile Ala Lys Glu Glu Met Ala Thr Glu Met Glu Arg Leu
255                 260                 265                 270 cgc ggc ctg cgt aac cgt ctg tgg aac ggc atc aaa gat atc gaa gaa    1465
Arg Gly Leu Arg Asn Arg Leu Trp Asn Gly Ile Lys Asp Ile Glu Glu
                275                 280                 285 gtt tac ctg aac ggt gac ctg gaa cac ggt gcg ccg aac att ctc aac    1513
Val Tyr Leu Asn Gly Asp Leu Glu His Gly Ala Pro Asn Ile Leu Asn
            290                 295                 300 gtc agc ttc aac tac gtt gaa ggt gag tcg ctg att atg gcg ctg aaa    1561
Val Ser Phe Asn Tyr Val Glu Gly Glu Ser Leu Ile Met Ala Leu Lys
        305                 310                 315 gac ctc gca gtt tct tca ggt tcc gcc tgt acg tca gca agc ctc gaa    1609
Asp Leu Ala Val Ser Ser Gly Ser Ala Cys Thr Ser Ala Ser Leu Glu
    320                 325                 330 ccg tcc tac gtg ctg cgc gcg ctg ggg ctg aac gac gag ctg gca cat    1657
Pro Ser Tyr Val Leu Arg Ala Leu Gly Leu Asn Asp Glu Leu Ala His
335                 340                 345                 350 agc tct atc cgt ttc tct tta ggt cgt ttt act act gaa gaa gag atc    1705
Ser Ser Ile Arg Phe Ser Leu Gly Arg Phe Thr Thr Glu Glu Glu Ile
                355                 360                 365 gac tac acc atc gag tta gtt cgt aaa tcc atc ggt cgt ctg cgt gac    1753
Asp Tyr Thr Ile Glu Leu Val Arg Lys Ser Ile Gly Arg Leu Arg Asp
            370                 375                 380 ctt tct ccg ctg tgg gaa atg tac aag cag ggc gtg gat ctg aac agc    1801
Leu Ser Pro Leu Trp Glu Met Tyr Lys Gln Gly Val Asp Leu Asn Ser
        385                 390                 395 atc gaa tgg gct cat cat taaacgcgtg ctagaggcat caaataaaac           1849
Ile Glu Trp Ala His His
            400 gaaaggctca gtcgaaagac tgggcctttc gttttatctg ttgtttgtcg gtgaacgctc  1909 tcctgagtag gacaaatccg ccgccctaga cctaggggat atattccgct tcctcgctca  1969 ctgactcgct acgctcggtc gttcgactgc ggcgagcgga aatggcttac gaacggggcg  2029
```

-continued

```
gagatttcct ggaagatgcc aggaagatac ttaacaggga agtgagaggg ccgcggcaaa    2089 gccgttttc cataggctcc gcccccctga caagcatcac gaaatctgac gctcaaatca    2149
gtggtggcga aacccgacag gactataaag ataccaggcg tttcccctg gcggctccct    2209 cgtgcgctct cctgttcctg cctttcggtt taccggtgtc attccgctgt tatggccgcg    2269
tttgtctcat tccacgcctg acactcagtt ccgggtaggc agttcgctcc aagctggact    2329
gtatgcacga accccccgtt cagtccgacc gctgcgcctt atccggtaac tatcgtcttg    2389
agtccaaccc ggaaagacat gcaaaagcac cactggcagc agccactggt aattgattta    2449
gaggagttag tcttgaagtc atgcgccggt taaggctaaa ctgaaaggac aagttttggt    2509
gactgcgctc ctccaagcca gttacctcgg ttcaaagagt tggtagctca gagaaccttc    2569
gaaaaaccgc cctgcaaggc ggttttttcg ttttcagagc aagagattac gcgcagacca    2629
aaacgatctc aagaagatca tcttattaat cagataaaat atttctagat ttcagtgcaa    2689
tttatctctt caaatgtagc acctgaagtc agccccatac gatataagtt gttactagtg    2749
cttggattct caccaataaa aaacgcccgg cggcaaccga gcgttctgaa caaatccaga    2809
tggagttctg aggtcattac tggatctatc aacaggagtc caagcgagct ctcgaacccc    2869
agagtcccgc tcagaagaac tcgtcaagaa ggcgatagaa ggcgatgcgc tgcgaatcgg    2929
gagcggcgat accgtaaagc acgaggaagc ggtcagccca ttcgccgcca agctcttcag    2989
caatatcacg ggtagccaac gctatgtcct gatagcggtc cgccacaccc agccggccac    3049
agtcgatgaa tccagaaaag cggccatttt ccaccatgat attcggcaag caggcatcgc    3109
catgggtcac gacgagatcc tcgccgtcgg gcatgcgcgc cttgagcctg gcgaacagtt    3169
cggctggcgc gagcccctga tgctcttcgt ccagatcatc ctgatcgaca agaccggctt    3229
ccatccgagt acgtgctcgc tcgatgcgat gtttcgcttg gtggtcgaat gggcaggtag    3289
ccggatcaag cgtatgcagc cgccgcattg catcagccat gatggatact ttctcggcag    3349
gagcaaggtg agatgacagg agatcctgcc ccggcactt cgcccaatagc agccagtccc    3409 ttcccgcttc agtgacaacg tcgagcacag ctgcgcaagg aacgcccgtc gtggccagcc    3469
acgatagccg cgctgcctcg tcctgcagtt cattcagggc accggacagg tcggtcttga    3529
caaaaagaac cgggcgcccc tgcgctgaca gccggaacac ggcggcatca gagcagccga    3589
ttgtctgttg tgcccagtca tagccgaata gcctctccac ccaagcggcc ggagaacctg    3649
cgtgcaatcc atcttgttca atcatgcgaa acgatcctca tcctgtctct tgatcagatc    3709
ttgatcccct gcgccatcag atccttggcg gcaagaaagc catccagttt actttgcagg    3769
gcttcccaac cttaccagag ggcgccccag ctggcaattc                           3810
```

<210> SEQ ID NO 8
<211> LENGTH: 404
<212> TYPE: PRT
<213> ORGANISM: clone pHS1bioS2

<400> SEQUENCE: 8

```
Met Lys Leu Pro Ile Tyr Leu Asp Tyr Ser Ala Thr Thr Pro Val Asp
  1               5                  10                  15

Pro Arg Val Ala Glu Lys Met Met Gln Phe Met Thr Met Asp Gly Thr
             20                  25                  30

Phe Gly Asn Pro Ala Ser Arg Ser His Arg Phe Gly Trp Gln Ala Glu
         35                  40                  45

Glu Ala Val Asp Ile Ala Arg Asn Gln Ile Ala Asp Leu Val Gly Ala
```

-continued

```
                        50                   55                   60
Asp Pro Arg Glu Ile Val Phe Thr Ser Gly Ala Thr Glu Ser Asp Asn
 65                   70                   75                   80
Leu Ala Ile Lys Gly Ala Ala Asn Phe Tyr Gln Lys Lys Gly Lys His
                 85                   90                   95
Ile Ile Thr Ser Lys Thr Glu His Lys Ala Val Leu Asp Thr Cys Arg
            100                  105                  110
Gln Leu Glu Arg Glu Gly Phe Glu Val Thr Tyr Leu Ala Pro Gln Arg
        115                  120                  125
Asn Gly Ile Ile Asp Leu Lys Glu Leu Glu Ala Ala Met Arg Asp Asp
    130                  135                  140
Thr Ile Leu Val Ser Ile Met His Val Asn Asn Glu Ile Gly Val Val
145                  150                  155                  160
Gln Asp Ile Ala Ala Ile Gly Glu Met Cys Arg Ala Arg Gly Ile Ile
                165                  170                  175
Tyr His Val Asp Ala Thr Gln Ser Val Gly Lys Leu Pro Ile Asp Leu
            180                  185                  190
Ser Gln Leu Lys Val Asp Leu Met Ser Phe Ser Gly His Lys Ile Tyr
        195                  200                  205
Gly Pro Lys Gly Ile Gly Ala Leu Tyr Val Arg Arg Lys Pro Arg Val
    210                  215                  220
Arg Ile Glu Ala Gln Met His Gly Gly His Glu Arg Gly Met Arg
225                  230                  235                  240
Ser Gly Thr Leu Pro Val His Gln Ile Val Gly Met Gly Glu Ala Tyr
                245                  250                  255
Arg Ile Ala Lys Glu Glu Met Ala Thr Glu Met Glu Arg Leu Arg Gly
            260                  265                  270
Leu Arg Asn Arg Leu Trp Asn Gly Ile Lys Asp Ile Glu Glu Val Tyr
        275                  280                  285
Leu Asn Gly Asp Leu Glu His Gly Ala Pro Asn Ile Leu Asn Val Ser
    290                  295                  300
Phe Asn Tyr Val Glu Gly Glu Ser Leu Ile Met Ala Leu Lys Asp Leu
305                  310                  315                  320
Ala Val Ser Ser Gly Ser Ala Cys Thr Ser Ala Ser Leu Glu Pro Ser
                325                  330                  335
Tyr Val Leu Arg Ala Leu Gly Leu Asn Asp Glu Leu Ala His Ser Ser
            340                  345                  350
Ile Arg Phe Ser Leu Gly Arg Phe Thr Thr Glu Glu Glu Ile Asp Tyr
        355                  360                  365
Thr Ile Glu Leu Val Arg Lys Ser Ile Gly Arg Leu Arg Asp Leu Ser
    370                  375                  380
Pro Leu Trp Glu Met Tyr Lys Gln Gly Val Asp Leu Asn Ser Ile Glu
385                  390                  395                  400
Trp Ala His His
```

<210> SEQ ID NO 9
<211> LENGTH: 3465
<212> TYPE: DNA
<213> ORGANISM: clone pHS2bioS1
<220> FEATURE:
<221> NAME/KEY: CDS
<222> LOCATION: 272...1477

<400> SEQUENCE: 9
gacgtctaag aaaccattat tatcatgaca ttaacctata aaaataggcg tatcacgagg    60

-continued

```
cccttccgtc ttcacctcga gtccctatca gtgatagaga ttgacatccc tatcagtgat    120
agagatactg agcacatcag caggacgcac tgaccgaatt cattaaagag gagaaaggta    180
ccgggccccc cctcgaggtc gacggtatcg ataagcttga tatcgaattc ctgcagcccg    240
ggggatccca tggtacgcgt cgaggagtac c atg aac gtt ttt aat ccc gcg       292
                                   Met Asn Val Phe Asn Pro Ala
                                    1               5 cag ttt cgc gcc cag ttt ccc gca cta cag gat gcg ggc gtc tat ctc      340
Gln Phe Arg Ala Gln Phe Pro Ala Leu Gln Asp Ala Gly Val Tyr Leu
         10                  15                  20 gac agc gcc gcg acc gcg ctt aaa cct gaa gcc gtg gtt gaa gcc acc      388
Asp Ser Ala Ala Thr Ala Leu Lys Pro Glu Ala Val Val Glu Ala Thr
 25                  30                  35 caa cag ttt tac agt ctg agc gcc gga aac gtc cat cgc agc cag ttt      436
Gln Gln Phe Tyr Ser Leu Ser Ala Gly Asn Val His Arg Ser Gln Phe
 40                  45                  50                  55 gcc gaa gcc caa cgc ctg acc gcg cgt tat gaa gct gca cga gag aaa      484
Ala Glu Ala Gln Arg Leu Thr Ala Arg Tyr Glu Ala Ala Arg Glu Lys
                 60                  65                  70 gtg gcg caa tta ctg aat gca ccg gat gat aaa act atc gtc tgg acg      532
Val Ala Gln Leu Leu Asn Ala Pro Asp Asp Lys Thr Ile Val Trp Thr
             75                  80                  85 cgc ggc acc act gaa tcc atc aac atg gtg gca caa tgc tat gcg cgt      580
Arg Gly Thr Thr Glu Ser Ile Asn Met Val Ala Gln Cys Tyr Ala Arg
         90                  95                 100 ccg cgt ctg caa ccg ggc gat gag att att gtc agc gtg gca gaa cac      628
Pro Arg Leu Gln Pro Gly Asp Glu Ile Ile Val Ser Val Ala Glu His
     105                 110                 115 cac gcc aac ctc gtc ccc tgg ctg atg gtc gcc caa caa act gga gcc      676
His Ala Asn Leu Val Pro Trp Leu Met Val Ala Gln Gln Thr Gly Ala
120                 125                 130                 135 aaa gtg gtg aaa ttg ccg ctt aat gcg cag cga ctg ccg gat gtc gat      724
Lys Val Val Lys Leu Pro Leu Asn Ala Gln Arg Leu Pro Asp Val Asp
                 140                 145                 150 ttg ttg cca gaa ctg att act ccc cgt agt cgg att ctg gcg ttg ggt      772
Leu Leu Pro Glu Leu Ile Thr Pro Arg Ser Arg Ile Leu Ala Leu Gly
             155                 160                 165 cag atg tcg aac gtt act ggc ggt tgc ccg gat ctg gcg cga gcg att      820
Gln Met Ser Asn Val Thr Gly Gly Cys Pro Asp Leu Ala Arg Ala Ile
         170                 175                 180 acc ttt gct cat tca gcc ggg atg gtg gtg atg gtt gat ggt gct cag      868
Thr Phe Ala His Ser Ala Gly Met Val Val Met Val Asp Gly Ala Gln
     185                 190                 195 ggg gca gtg cat ttc ccc gcg gat gtt cag caa ctg gat att gat ttc      916
Gly Ala Val His Phe Pro Ala Asp Val Gln Gln Leu Asp Ile Asp Phe
200                 205                 210                 215 tat gct ttt tca ggt cac aaa ctg tat ggc ccg aca ggt atc ggc gtg      964
Tyr Ala Phe Ser Gly His Lys Leu Tyr Gly Pro Thr Gly Ile Gly Val
                 220                 225                 230 ctg tat ggt aaa tca gaa ctg ctg gag gcg atg tcg ccc tgg ctg ggc     1012
Leu Tyr Gly Lys Ser Glu Leu Leu Glu Ala Met Ser Pro Trp Leu Gly
             235                 240                 245 ggc ggc aaa atg gtt cac gaa gtg agt ttt gac ggc ttc acg act caa     1060
Gly Gly Lys Met Val His Glu Val Ser Phe Asp Gly Phe Thr Thr Gln
         250                 255                 260 tct gcg ccg tgg aaa ctg gaa gct gga acg cca aat gtc gct ggt gtc     1108
Ser Ala Pro Trp Lys Leu Glu Ala Gly Thr Pro Asn Val Ala Gly Val
     265                 270                 275
```

```
ata gga tta agc gcg gcg ctg gaa tgg ctg gca gat tac gat atc aac      1156
Ile Gly Leu Ser Ala Ala Leu Glu Trp Leu Ala Asp Tyr Asp Ile Asn
280                 285                 290                 295 cag gcc gaa agc tgg agc cgt agc tta gca acg ctg gcg gaa gat gcg      1204
Gln Ala Glu Ser Trp Ser Arg Ser Leu Ala Thr Leu Ala Glu Asp Ala
                300                 305                 310 ctg gcg aaa cgt ccc ggc ttt cgt tca ttc cgc tgc cag gat tcc agc      1252
Leu Ala Lys Arg Pro Gly Phe Arg Ser Phe Arg Cys Gln Asp Ser Ser
            315                 320                 325 ctg ctg gcc ttt gat ttt gct ggc gtt cat cat agc gat atg gtg acg      1300
Leu Leu Ala Phe Asp Phe Ala Gly Val His His Ser Asp Met Val Thr
        330                 335                 340 ctg ctg gcg gag tac ggt att gcc ctg cgg gcc ggg cag cat tgc gct      1348
Leu Leu Ala Glu Tyr Gly Ile Ala Leu Arg Ala Gly Gln His Cys Ala
    345                 350                 355 cag ccg cta ctg gca gaa tta ggc gta acc ggc aca ctg cgc gcc tct      1396
Gln Pro Leu Leu Ala Glu Leu Gly Val Thr Gly Thr Leu Arg Ala Ser
360                 365                 370                 375 ttt gcg cca tat aat aca aag agt gat gtg gat gcg ctg gtg aat gcc      1444
Phe Ala Pro Tyr Asn Thr Lys Ser Asp Val Asp Ala Leu Val Asn Ala
                380                 385                 390 gtt gac cgc gcg ctg gaa tta ttg gtg gat taaacgcgtg ctagaggcat       1494
Val Asp Arg Ala Leu Glu Leu Leu Val Asp
            395                 400 caaataaaac gaaaggctca gtcgaaagac tgggcctttc gttttatctg ttgtttgtcg    1554
gtgaacgctc tcctgagtag gacaaatccg ccgccctaga cctaggggat atattccgct    1614
tcctcgctca ctgactcgct acgctcggtc gttcgactgc ggcgagcgga aatggcttac    1674
gaacggggcg gagatttcct ggaagatgcc aggaagatac ttaacaggga agtgagaggg    1734
ccgcggcaaa gccgttttc cataggctcc gccccctga caagcatcac gaaatctgac     1794
gctcaaatca gtggtggcga aacccgacag gactataaag ataccaggcg tttccccctg   1854
gcggctccct cgtgcgctct cctgttcctg cctttcggtt taccggtgtc attccgctgt   1914
tatggccgcg tttgtctcat ccacgcctg acactcagtt ccgggtaggc agttcgctcc    1974
aagctggact gtatgcacga accccccgtt cagtccgacc gctgcgcctt atccggtaac   2034
tatcgtcttg agtccaaccc ggaaagacat gcaaaagcac cactggcagc agccactggt   2094
aattgattta gaggagttag tcttgaagtc atgcgccggt taaggctaaa ctgaaaggac   2154
aagttttggt gactgcgctc ctccaagcca gttacctcgg ttcaaagagt tggtagctca   2214
gagaaccttc gaaaaaccgc cctgcaaggc ggttttttcg ttttcagagc aagagattac   2274
gcgcagacca aaacgatctc aagaagatca tcttattaat cagataaaat atttctagat   2334
ttcagtgcaa tttatctctt caaatgtagc acctgaagtc agccccatac gataagtt    2394
gttactagtg cttggattct caccaataaa aaacgcccgg cggcaaccga gcgttctgaa   2454
caaatccaga tggagttctg aggtcattac tggatctatc aacaggagtc caagcgagct   2514
ctcgaacccc agagtcccgc tcagaagaac tcgtcaagaa ggcgatagaa ggcgatgcgc   2574
tgcgaatcgg gagcggcgat accgtaaagc acgaggaagc ggtcagccca ttcgccgcca   2634
agctcttcag caatatcacg ggtagccaac gctatgtcct gatagcggtc cgccacaccc   2694
agccggccac agtcgatgaa tccagaaaag cggccatttt ccaccatgat attcggcaag   2754
caggcatcgc catgggtcac gacgagatcc tcgccgtcgg gcatgcgcgc cttgagcctg   2814
gcgaacagtt cggctggcgc gagcccctga tgctcttcgt ccagatcatc ctgatcgaca   2874
agaccggctt ccatccgagt acgtgctcgc tcgatgcgat gtttcgcttg gtggtcgaat   2934
```

-continued

```
gggcaggtag ccggatcaag cgtatgcagc cgccgcattg catcagccat gatggatact    2994
ttctcggcag gagcaaggtg agatgacagg agatcctgcc ccggcacttc gcccaatagc    3054
agccagtccc ttcccgcttc agtgacaacg tcgagcacag ctgcgcaagg aacgcccgtc    3114
gtggccagcc acgatagccg cgctgcctcg tcctgcagtt cattcagggc accggacagg    3174
tcggtcttga caaaaagaac cgggcgcccc tgcgctgaca gccggaacac ggcggcatca    3234
gagcagccga ttgtctgttg tgcccagtca tagccgaata gcctctccac ccaagcggcc    3294
ggagaacctg cgtgcaatcc atcttgttca atcatgcgaa acgatcctca tcctgtctct    3354
tgatcagatc ttgatcccct gcgccatcag atccttggcg gcaagaaagc catccagttt    3414
actttgcagg gcttcccaac cttaccagag ggcgccccag ctggcaattc c              3465
```

<210> SEQ ID NO 10
<211> LENGTH: 401
<212> TYPE: PRT
<213> ORGANISM: clone pHS2bioS1

<400> SEQUENCE: 10

```
Met Asn Val Phe Asn Pro Ala Gln Phe Arg Ala Gln Phe Pro Ala Leu
  1               5                  10                  15

Gln Asp Ala Gly Val Tyr Leu Asp Ser Ala Ala Thr Ala Leu Lys Pro
             20                  25                  30

Glu Ala Val Val Glu Ala Thr Gln Gln Phe Tyr Ser Leu Ser Ala Gly
         35                  40                  45

Asn Val His Arg Ser Gln Phe Ala Glu Ala Gln Arg Leu Thr Ala Arg
     50                  55                  60

Tyr Glu Ala Ala Arg Glu Lys Val Ala Gln Leu Leu Asn Ala Pro Asp
 65                  70                  75                  80

Asp Lys Thr Ile Val Trp Thr Arg Gly Thr Thr Glu Ser Ile Asn Met
                 85                  90                  95

Val Ala Gln Cys Tyr Ala Arg Pro Arg Leu Gln Pro Gly Asp Glu Ile
            100                 105                 110

Ile Val Ser Val Ala Glu His His Ala Asn Leu Val Pro Trp Leu Met
        115                 120                 125

Val Ala Gln Gln Thr Gly Ala Lys Val Val Lys Leu Pro Leu Asn Ala
    130                 135                 140

Gln Arg Leu Pro Asp Val Asp Leu Leu Pro Glu Leu Ile Thr Pro Arg
145                 150                 155                 160

Ser Arg Ile Leu Ala Leu Gly Gln Met Ser Asn Val Thr Gly Gly Cys
                165                 170                 175

Pro Asp Leu Ala Arg Ala Ile Thr Phe Ala His Ser Ala Gly Met Val
            180                 185                 190

Val Met Val Asp Gly Ala Gln Gly Ala Val His Phe Pro Ala Asp Val
        195                 200                 205

Gln Gln Leu Asp Ile Asp Phe Tyr Ala Phe Ser Gly His Lys Leu Tyr
    210                 215                 220

Gly Pro Thr Gly Ile Gly Val Leu Tyr Gly Lys Ser Glu Leu Leu Glu
225                 230                 235                 240

Ala Met Ser Pro Trp Leu Gly Gly Gly Lys Met Val His Glu Val Ser
                245                 250                 255

Phe Asp Gly Phe Thr Thr Gln Ser Ala Pro Trp Lys Leu Glu Ala Gly
            260                 265                 270

Thr Pro Asn Val Ala Gly Val Ile Gly Leu Ser Ala Ala Leu Glu Trp
```

```
                        275                 280                 285
Leu Ala Asp Tyr Asp Ile Asn Gln Ala Glu Ser Trp Ser Arg Ser Leu
            290                 295                 300

Ala Thr Leu Ala Glu Asp Ala Leu Ala Lys Arg Pro Gly Phe Arg Ser
305                 310                 315                 320

Phe Arg Cys Gln Asp Ser Ser Leu Leu Ala Phe Asp Phe Ala Gly Val
                325                 330                 335

His His Ser Asp Met Val Thr Leu Leu Ala Glu Tyr Gly Ile Ala Leu
            340                 345                 350

Arg Ala Gly Gln His Cys Ala Gln Pro Leu Leu Ala Glu Leu Gly Val
            355                 360                 365

Thr Gly Thr Leu Arg Ala Ser Phe Ala Pro Tyr Asn Thr Lys Ser Asp
            370                 375                 380

Val Asp Ala Leu Val Asn Ala Val Asp Arg Ala Leu Glu Leu Leu Val
385                 390                 395                 400

Asp

<210> SEQ ID NO 11
<211> LENGTH: 3481
<212> TYPE: DNA
<213> ORGANISM: clone pHS2bioS2
<220> FEATURE:
<221> NAME/KEY: CDS
<222> LOCATION: 279...1493

<400> SEQUENCE: 11
gacgtctaag aaaccattat tatcatgaca ttaacctata aaaataggcg tatcacgagg    60 cccttttcgtc ttcacctcga gtccctatca gtgatagaga ttgacatccc tatcagtgat   120
agagatactg agcacatcag caggacgcac tgaccgaatt cattaaagag gagaaaggta   180
ccgggccccc cctcgaggtc gacggtatcg ataagcttga tatcgaattc ctgcagcccg   240
ggggatccca tggtacgcgt aaagaggaga aattaact atg aaa tta ccg att       293
                                          Met Lys Leu Pro Ile
                                            1               5 tat ctc gac tac tcc gca acc acg ccg gtg gac ccg cgt gtt gcc gag     341
Tyr Leu Asp Tyr Ser Ala Thr Thr Pro Val Asp Pro Arg Val Ala Glu
                 10                  15                  20 aaa atg atg cag ttt atg acg atg gac gga acc ttt ggt aac ccg gcc     389
Lys Met Met Gln Phe Met Thr Met Asp Gly Thr Phe Gly Asn Pro Ala
              25                  30                  35 tcc cgt tct cac cgt ttc ggc tgg cag gct gaa gaa gcg gta gat atc     437
Ser Arg Ser His Arg Phe Gly Trp Gln Ala Glu Glu Ala Val Asp Ile
          40                  45                  50 gcc cgt aat cag att gcc gat ctg gtc ggc gct gat ccg cgt gaa atc     485
Ala Arg Asn Gln Ile Ala Asp Leu Val Gly Ala Asp Pro Arg Glu Ile
      55                  60                  65 gtc ttt acc tct ggt gca acc gaa tct gac aac ctg gcg atc aaa ggt     533
Val Phe Thr Ser Gly Ala Thr Glu Ser Asp Asn Leu Ala Ile Lys Gly
  70                  75                  80                  85 gca gcc aac ttt tat cag aaa aaa ggc aag cac atc atc acc agc aaa     581
Ala Ala Asn Phe Tyr Gln Lys Lys Gly Lys His Ile Ile Thr Ser Lys
                 90                  95                 100 acc gaa cac aaa gcg gta ctg gat acc tgc cgt cag ctg gag cgc gaa     629
Thr Glu His Lys Ala Val Leu Asp Thr Cys Arg Gln Leu Glu Arg Glu
             105                 110                 115 ggt ttt gaa gtc acc tac ctg gca ccg cag cgt aac ggc att atc gac     677
Gly Phe Glu Val Thr Tyr Leu Ala Pro Gln Arg Asn Gly Ile Ile Asp
         120                 125                 130
```

-continued

```
ctg aaa gaa ctt gaa gca gcg atg cgt gac gac acc atc ctc gtg tcc        725
Leu Lys Glu Leu Glu Ala Ala Met Arg Asp Asp Thr Ile Leu Val Ser
    135                 140                 145 atg cac gta aat aac gaa atc ggc gtg gtg cag gat atc gcg gct            773
Ile Met His Val Asn Asn Glu Ile Gly Val Val Gln Asp Ile Ala Ala
150                 155                 160                 165 atc ggc gaa atg tgc cgt gct cgt ggc att atc tat cac gtt gat gca        821
Ile Gly Glu Met Cys Arg Ala Arg Gly Ile Ile Tyr His Val Asp Ala
                170                 175                 180 acc cag agc gtg ggt aaa ctg cct atc gac ctg agc cag ttg aaa gtt        869
Thr Gln Ser Val Gly Lys Leu Pro Ile Asp Leu Ser Gln Leu Lys Val
            185                 190                 195 gac ctg atg tct ttc tcc ggt cac aaa atc tat ggc ccg aaa ggt atc        917
Asp Leu Met Ser Phe Ser Gly His Lys Ile Tyr Gly Pro Lys Gly Ile
        200                 205                 210 ggt gcg ctg tat gta cgt cgt aaa ccg cgc gta cgc atc gaa gcg caa        965
Gly Ala Leu Tyr Val Arg Arg Lys Pro Arg Val Arg Ile Glu Ala Gln
    215                 220                 225 atg cac ggc ggc ggt cac gag cgc ggt atg cgt tcc ggc act ctg cct       1013
Met His Gly Gly Gly His Glu Arg Gly Met Arg Ser Gly Thr Leu Pro
230                 235                 240                 245 gtt cac cag atc gtc gga atg ggc gag gcc tat cgc atc gca aaa gaa       1061
Val His Gln Ile Val Gly Met Gly Glu Ala Tyr Arg Ile Ala Lys Glu
                250                 255                 260 gag atg gcg acc gag atg gaa cgt ctg cgc ggc ctg cgt aac cgt ctg       1109
Glu Met Ala Thr Glu Met Glu Arg Leu Arg Gly Leu Arg Asn Arg Leu
            265                 270                 275 tgg aac ggc atc aaa gat atc gaa gaa gtt tac ctg aac ggt gac ctg       1157
Trp Asn Gly Ile Lys Asp Ile Glu Glu Val Tyr Leu Asn Gly Asp Leu
        280                 285                 290 gaa cac ggt gcg ccg aac att ctc aac gtc agc ttc aac tac gtt gaa       1205
Glu His Gly Ala Pro Asn Ile Leu Asn Val Ser Phe Asn Tyr Val Glu
    295                 300                 305 ggt gag tcg ctg att atg gcg ctg aaa gac ctc gca gtt tct tca ggt       1253
Gly Glu Ser Leu Ile Met Ala Leu Lys Asp Leu Ala Val Ser Ser Gly
310                 315                 320                 325 tcc gcc tgt acg tca gca agc ctc gaa ccg tcc tac gtg ctg cgc gcg       1301
Ser Ala Cys Thr Ser Ala Ser Leu Glu Pro Ser Tyr Val Leu Arg Ala
                330                 335                 340 ctg ggg ctg aac gac gag ctg gca cat agc tct atc cgt ttc tct tta       1349
Leu Gly Leu Asn Asp Glu Leu Ala His Ser Ser Ile Arg Phe Ser Leu
            345                 350                 355 ggt cgt ttt act act gaa gaa gag atc gac tac acc atc gag tta gtt       1397
Gly Arg Phe Thr Thr Glu Glu Glu Ile Asp Tyr Thr Ile Glu Leu Val
        360                 365                 370 cgt aaa tcc atc ggt cgt ctg cgt gac ctt tct ccg ctg tgg gaa atg       1445
Arg Lys Ser Ile Gly Arg Leu Arg Asp Leu Ser Pro Leu Trp Glu Met
    375                 380                 385 tac aag cag ggc gtg gat ctg aac agc atc gaa tgg gct cat cat           1500
taaacgcgtg Tyr Lys Gln Gly Val Asp Leu Asn Ser Ile Glu Trp Ala His His
390                 395                 400 ctagaggcat caaataaaac gaaaggctca gtcgaaagac tgggcctttc gttttatctg     1560
ttgtttgtcg gtgaacgctc tcctgagtag gacaaatccg ccgccctaga cctaggggat     1620
atattccgct tcctcgctca ctgactcgct acgctcggtc gttcgactgc ggcgagcgga     1680
aatggcttac gaacggggcg agatttcct ggaagatgcc aggaagatac ttaacaggga      1740
```

-continued

```
agtgagaggg ccgcggcaaa gccgttttc cataggctcc gccccctga caagcatcac    1800
gaaatctgac gctcaaatca gtggtggcga aacccgacag gactataaag ataccaggcg   1860
tttcccctg gcggctccct cgtgcgctct cctgttcctg cctttcggtt taccggtgtc    1920
attccgctgt tatggccgcg tttgtctcat tccacgcctg acactcagtt ccgggtaggc   1980
agttcgctcc aagctggact gtatgcacga accccccgtt cagtccgacc gctgcgcctt   2040
atccggtaac tatcgtcttg agtccaaccc ggaaagacat gcaaaagcac cactggcagc   2100
agccactggt aattgattta gaggagttag tcttgaagtc atgcgccggt taaggctaaa   2160
ctgaaaggac aagttttggt gactgcgctc ctccaagcca gttacctcgg ttcaaagagt   2220
tggtagctca gagaaccttc gaaaaaccgc cctgcaaggc ggttttttcg ttttcagagc   2280
aagagattac gcgcagacca aaacgatctc aagaagatca tcttattaat cagataaaat   2340
atttctagat ttcagtgcaa tttatctctt caaatgtagc acctgaagtc agccccatac   2400
gatataagtt gttactagtg cttggattct caccaataaa aaacgcccgg cggcaaccga   2460
gcgttctgaa caaatccaga tggagttctg aggtcattac tggatctatc aacaggagtc   2520
caagcgagct ctcgaacccc agagtcccgc tcagaagaac tcgtcaagaa ggcgatagaa   2580
ggcgatgcgc tgcgaatcgg gagcggcgat accgtaaagc acgaggaagc ggtcagccca   2640
ttcgccgcca agctcttcag caatatcacg ggtagccaac gctatgtcct gatagcggtc   2700
cgccacaccc agccggccac agtcgatgaa tccagaaaag cggccatttt ccaccatgat   2760
attcggcaag caggcatcgc catgggtcac gacgagatcc tcgccgtcgg gcatgcgcgc   2820
cttgagcctg gcgaacagtt cggctggcgc gagcccctga tgctcttcgt ccagatcatc   2880
ctgatcgaca agaccggctt ccatccgagt acgtgctcgc tcgatgcgat gtttcgcttg   2940
gtggtcgaat gggcaggtag ccggatcaag cgtatgcagc cgccgcattg catcagccat   3000
gatggatact ttctcggcag gagcaaggtg agatgacagg agatcctgcc ccggcacttc   3060
gcccaatagc agccagtccc ttcccgcttc agtgacaacg tcgagcacag ctgcgcaagg   3120
aacgcccgtc gtggccagcc acgatagccg cgctgcctcg tcctgcagtt cattcagggc   3180
accggacagg tcggtcttga caaaaagaac cgggcgcccc tgcgctgaca gccgaacac    3240
ggcggcatca gagcagccga ttgtctgttg tgcccagtca tagccgaata gcctctccac   3300
ccaagcggcc ggagaacctg cgtgcaatcc atcttgttca atcatgcgaa acgatcctca   3360
tcctgtctct tgatcagatc ttgatcccct gcgccatcag atccttggcg gcaagaaagc   3420
catccagttt actttgcagg gcttcccaac cttaccagag ggcgccccag ctggcaattc   3480
c                                                                   3481
```

<210> SEQ ID NO 12
<211> LENGTH: 404
<212> TYPE: PRT
<213> ORGANISM: clone pHS2bioS2

<400> SEQUENCE: 12

```
Met Lys Leu Pro Ile Tyr Leu Asp Tyr Ser Ala Thr Thr Pro Val Asp
 1               5                  10                  15

Pro Arg Val Ala Glu Lys Met Met Gln Phe Met Thr Met Asp Gly Thr
                20                  25                  30

Phe Gly Asn Pro Ala Ser Arg Ser His Arg Phe Gly Trp Gln Ala Glu
            35                  40                  45

Glu Ala Val Asp Ile Ala Arg Asn Gln Ile Ala Asp Leu Val Gly Ala
```

```
              50                  55                  60
Asp Pro Arg Glu Ile Val Phe Thr Ser Gly Ala Thr Glu Ser Asp Asn
 65                  70                  75                  80

Leu Ala Ile Lys Gly Ala Ala Asn Phe Tyr Gln Lys Lys Gly Lys His
                 85                  90                  95

Ile Ile Thr Ser Lys Thr Glu His Lys Ala Val Leu Asp Thr Cys Arg
            100                 105                 110

Gln Leu Glu Arg Glu Gly Phe Glu Val Thr Tyr Leu Ala Pro Gln Arg
        115                 120                 125

Asn Gly Ile Ile Asp Leu Lys Glu Leu Glu Ala Ala Met Arg Asp Asp
130                 135                 140

Thr Ile Leu Val Ser Ile Met His Val Asn Asn Glu Ile Gly Val Val
145                 150                 155                 160

Gln Asp Ile Ala Ala Ile Gly Glu Met Cys Arg Ala Arg Gly Ile Ile
                165                 170                 175

Tyr His Val Asp Ala Thr Gln Ser Val Gly Lys Leu Pro Ile Asp Leu
            180                 185                 190

Ser Gln Leu Lys Val Asp Leu Met Ser Phe Ser Gly His Lys Ile Tyr
        195                 200                 205

Gly Pro Lys Gly Ile Gly Ala Leu Tyr Val Arg Arg Lys Pro Arg Val
210                 215                 220

Arg Ile Glu Ala Gln Met His Gly Gly His Glu Arg Gly Met Arg
225                 230                 235                 240

Ser Gly Thr Leu Pro Val His Gln Ile Val Gly Met Gly Glu Ala Tyr
                245                 250                 255

Arg Ile Ala Lys Glu Glu Met Ala Thr Glu Met Glu Arg Leu Arg Gly
            260                 265                 270

Leu Arg Asn Arg Leu Trp Asn Gly Ile Lys Asp Ile Glu Glu Val Tyr
        275                 280                 285

Leu Asn Gly Asp Leu Glu His Gly Ala Pro Asn Ile Leu Asn Val Ser
290                 295                 300

Phe Asn Tyr Val Glu Gly Glu Ser Leu Ile Met Ala Leu Lys Asp Leu
305                 310                 315                 320

Ala Val Ser Ser Gly Ser Ala Cys Thr Ser Ala Ser Leu Glu Pro Ser
                325                 330                 335

Tyr Val Leu Arg Ala Leu Gly Leu Asn Asp Glu Leu Ala His Ser Ser
            340                 345                 350

Ile Arg Phe Ser Leu Gly Arg Phe Thr Thr Glu Glu Glu Ile Asp Tyr
        355                 360                 365

Thr Ile Glu Leu Val Arg Lys Ser Ile Gly Arg Leu Arg Asp Leu Ser
370                 375                 380

Pro Leu Trp Glu Met Tyr Lys Gln Gly Val Asp Leu Asn Ser Ile Glu
385                 390                 395                 400

Trp Ala His His

<210> SEQ ID NO 13
<211> LENGTH: 31
<212> TYPE: DNA
<213> ORGANISM: Oligonucleotide P15A,1
<220> FEATURE:
<221> NAME/KEY: misc_feature
<222> LOCATION: 1...31

<400> SEQUENCE: 13
ggcccctagg ggatatattc cgcttcctcg c                              31
```

<210> SEQ ID NO 14
<211> LENGTH: 31
<212> TYPE: DNA
<213> ORGANISM: Oligonucleotide P15A,2
<220> FEATURE:
<221> NAME/KEY: misc_feature
<222> LOCATION: 1...31

<400> SEQUENCE: 14
ggccactagt aacaacttat atcgtatggg g                          31

<210> SEQ ID NO 15
<211> LENGTH: 30
<212> TYPE: DNA
<213> ORGANISM: Oligonucleotide Kan-R,1
<220> FEATURE:
<221> NAME/KEY: misc_feature
<222> LOCATION: 1...30

<400> SEQUENCE: 15
ggccgagctc tcgaacccca gagtcccgct                            30

<210> SEQ ID NO 16
<211> LENGTH: 30
<212> TYPE: DNA
<213> ORGANISM: Oligonucleotide Kan-R,2
<220> FEATURE:
<221> NAME/KEY: misc_feature
<222> LOCATION: 1...30

<400> SEQUENCE: 16
ggccgacgtc ggaattgcca gctggggcgc                            30

<210> SEQ ID NO 17
<211> LENGTH: 30
<212> TYPE: DNA
<213> ORGANISM: Oligonucleotide T0,1
<220> FEATURE:
<221> NAME/KEY: misc_feature
<222> LOCATION: 1...30

<400> SEQUENCE: 17
ggccgagctc gcttggactc ctgttgatag                            30

<210> SEQ ID NO 18
<211> LENGTH: 39
<212> TYPE: DNA
<213> ORGANISM: Oligonucleotide T0,2
<220> FEATURE:
<221> NAME/KEY: misc_feature
<222> LOCATION: 1...39

<400> SEQUENCE: 18
ggccactagt gcttggattc tcaccaataa aaaacgccc                  39

<210> SEQ ID NO 19
<211> LENGTH: 31
<212> TYPE: DNA
<213> ORGANISM: Oligonucleotide T1,1
<220> FEATURE:
<221> NAME/KEY: misc_feature
<222> LOCATION: 1...31

<400> SEQUENCE: 19
ggcccctagg tctagggcgg cggatttgtc c                          31

<210> SEQ ID NO 20
<211> LENGTH: 32
<212> TYPE: DNA
<213> ORGANISM: Oligonucleotide T1,2
<220> FEATURE:
<221> NAME/KEY: misc_feature
<222> LOCATION: 1...32

<400> SEQUENCE: 20
ggcctctaga ggcatcaaat aaaacgaaag gc                                32

<210> SEQ ID NO 21
<211> LENGTH: 118
<212> TYPE: DNA
<213> ORGANISM: Oligonucleotide PPHS1,1
<220> FEATURE:
<221> NAME/KEY: misc_feature
<222> LOCATION: 1...118

<400> SEQUENCE: 21
tcgagatagc attttatcc ataagattag ccgatcctaa ggtttacaat tgtgagcgct    60
cacaattatg atagattcaa ttgtgagcgg ataacaattt cacacacgct agcggtac    118

<210> SEQ ID NO 22
<211> LENGTH: 110
<212> TYPE: DNA
<213> ORGANISM: Oligonucleotide PPHS1,2
<220> FEATURE:
<221> NAME/KEY: misc_feature
<222> LOCATION: 1...110

<400> SEQUENCE: 22
cgctagcgtg tgtgaaattg ttatccgctc acaattgaat ctatcataat tgtgagcgct    60
cacaattgta aaccttagga tcggctaatc ttatggataa aaatgctatc                110

<210> SEQ ID NO 23
<211> LENGTH: 79
<212> TYPE: DNA
<213> ORGANISM: Oligonucleotide PPHS2,1
<220> FEATURE:
<221> NAME/KEY: misc_feature
<222> LOCATION: 1...79

<400> SEQUENCE: 23
aattctccct atcagtgata gagattgaca tccctatcag tgatagagat actgagacat    60
caccaggacg cactgaccg                                                  79

<210> SEQ ID NO 24
<211> LENGTH: 80
<212> TYPE: DNA
<213> ORGANISM: Oligonucleotide PPHS2,2
<220> FEATURE:
<221> NAME/KEY: misc_feature
<222> LOCATION: 1...80

<400> SEQUENCE: 24
aattcggtca gtgcgtcctg gtgatgtctc agtatctcta tcactgatag ggatgtcaat    60
ctctatcact gatagggagg                                                80

<210> SEQ ID NO 25
<211> LENGTH: 78
<212> TYPE: DNA
<213> ORGANISM: Oligonucleotide PMCS1,1
<220> FEATURE:

```
<221> NAME/KEY: misc_feature
<222> LOCATION: 1...78

<400> SEQUENCE: 25
gtaccgggcc cccctcgag gtcgacggta tcgataagct tgatatcgaa ttcctgcagc      60
ccgggggatc ccatggta                                                   78

<210> SEQ ID NO 26
<211> LENGTH: 84
<212> TYPE: DNA
<213> ORGANISM: Oligonucleotide PMCS1,2
<220> FEATURE:
<221> NAME/KEY: misc_feature
<222> LOCATION: 1...84

<400> SEQUENCE: 26
acgcgtacca tgggatcccc cgggctgcag gaattcgata tcaagcttat cgataccgtc      60
gacctcgagg ggggcccgg tacc                                              84

<210> SEQ ID NO 27
<211> LENGTH: 27
<212> TYPE: DNA
<213> ORGANISM: Oligonucleotide PbioS1,1
<220> FEATURE:
<221> NAME/KEY: misc_feature
<222> LOCATION: 1...27

<400> SEQUENCE: 27
cgcacgcgtg aggagtacca tgaacgt                                          27

<210> SEQ ID NO 28
<211> LENGTH: 26
<212> TYPE: DNA
<213> ORGANISM: Oligonucleotide PbioS1,2
<220> FEATURE:
<221> NAME/KEY: misc_feature
<222> LOCATION: 1...26

<400> SEQUENCE: 28
cgcacgcgtt taatccacca ataatt                                           26

<210> SEQ ID NO 29
<211> LENGTH: 10
<212> TYPE: PRT
<213> ORGANISM: A. vinelandii
<220> FEATURE:
<221> NAME/KEY: misc_feature
<222> LOCATION: 7..7
<223> OTHER INFORMATION: Xaa is unknown.  Amino acid sequence is a
      typical N-terminal sequence of proteins of the NifS family.

<400> SEQUENCE: 29

Met Ile Tyr Leu Asp Asn Xaa Ala Thr Thr
                5                   10

<210> SEQ ID NO 30
<211> LENGTH: 12
<212> TYPE: PRT
<213> ORGANISM: E. coli

<400> SEQUENCE: 30

Met Lys Leu Pro Ile Tyr Leu Asp Tyr Ser Ala Thr
                5                   10

<210> SEQ ID NO 31
```

```
<211> LENGTH: 35
<212> TYPE: DNA
<213> ORGANISM: Oligonucleotide PbioS2,1
<220> FEATURE:
<221> NAME/KEY: misc_feature
<222> LOCATION: 1...35
<223> OTHER INFORMATION: n represents g, a, t or c

<400> SEQUENCE: 31
atgaarytnc cnathtayyt ngaytaywsn gcnac                          35

<210> SEQ ID NO 32
<211> LENGTH: 29
<212> TYPE: DNA
<213> ORGANISM: Oligonucleotide PbioS2,2
<220> FEATURE:
<221> NAME/KEY: misc_feature
<222> LOCATION: 1...29

<400> SEQUENCE: 32
cccaghggrc crtgcagytt rtgrccrga                                 29

<210> SEQ ID NO 33
<211> LENGTH: 30
<212> TYPE: DNA
<213> ORGANISM: Oligonucleotide PbioS2,3
<220> FEATURE:
<221> NAME/KEY: misc_feature
<222> LOCATION: 1...30

<400> SEQUENCE: 33
gcgtgggtaa actgcctatc gacctgagcc                                30

<210> SEQ ID NO 34
<211> LENGTH: 29
<212> TYPE: DNA
<213> ORGANISM: Oligonucleotide PbioS2,4
<220> FEATURE:
<221> NAME/KEY: misc_feature
<222> LOCATION: 1...29

<400> SEQUENCE: 34
ctacgcttcc ttcagcctgc cagccgaaa                                 29

<210> SEQ ID NO 35
<211> LENGTH: 50
<212> TYPE: DNA
<213> ORGANISM: Oligonucleotide PbioS2,5
<220> FEATURE:
<221> NAME/KEY: misc_feature
<222> LOCATION: 1...50

<400> SEQUENCE: 35
catgacgcgt aaagaggaga aattaactat gaaattaccg atttatttgg           50

<210> SEQ ID NO 36
<211> LENGTH: 27
<212> TYPE: DNA
<213> ORGANISM: Oligonucleotide PbioS2,6
<220> FEATURE:
<221> NAME/KEY: misc_feature
<222> LOCATION: 1...27

<400> SEQUENCE: 36
gcgacgcgtg attaatgatg agcccat                                   27

<210> SEQ ID NO 37
```

```
<211> LENGTH: 33
<212> TYPE: DNA
<213> ORGANISM: Oligonucleotide Pbio1,1
<220> FEATURE:
<221> NAME/KEY: misc_feature
<222> LOCATION: 1...33

<400> SEQUENCE: 37
aataaggaat tcttatgtac tttccggttg ccg                              33

<210> SEQ ID NO 38
<211> LENGTH: 23
<212> TYPE: DNA
<213> ORGANISM: Oligonucleotide Pbio1,2
<220> FEATURE:
<221> NAME/KEY: misc_feature
<222> LOCATION: 1...23

<400> SEQUENCE: 38
aacagcagcc tgcagctgga tta                                        23
```

METHOD FOR PRODUCING BIOTIN

This application is a 371 of International Application No. PCT/EP98/04097 published as WO 99/05285 which has an international filing date of Jul. 2, 1998.

FIELD OF THE INVENTION

The invention relates to a gene construct comprising a biotin gene having the sequence SEQ ID No. 1 or SEQ ID No. 3, to organisms which comprise this gene construct, to the use of these sequences or of the gene construct for preparing biotin, and to a process for preparing biotin.

BACKGROUND OF THE INVENTION

Biotin (vitamin H) plays an essential role as coenzyme in enzyme-catalyzed carboxylation and decarboxylation reactions. Biotin is thus an essential factor in living cells. Almost all animals and some microorganisms have to take biotin in from the outside because they are unable to synthesize biotin themselves. It is thus an essential vitamin for these organisms. Bacteria, yeasts and plants by contrast are themselves able to synthesize biotin from precursors (Brown et al. Biotechnol. Genet. Eng. Rev. 9, 1991: 295–326, DeMoll, E., *Escherichia coli* and Salmonella, eds. Neidhardt, F. C. et al. ASM Press, Washington D.C., USA, 1996: 704–708, ISBN 1-55581-084-5).

Biotin synthesis has been investigated in bacterial organisms, specifically in the Gram-negative bacterium *Escherichia coli* and in the Gram-positive bacterium *Bacillus sphaericus* (Brown et al. Biotechnol. Genet. Eng. Rev. 9, 1991: 295–326). The first intermediate known to date in *E. coli* is regarded as being pimelyl-CoA (Pm-CoA), which derives from fatty acid synthesis (DeMoll, E., *Escherichia coli* and Salmonella, eds. Neidhardt, F. C. et al. ASM Press, Washington D.C., USA, 1996: 704–708, ISBN 1-55581-084-5 1996). The synthetic pathway for this biotin precursor in *E. coli* is substantially unknown at present (Ifuku 1993, Lemoine 1996). Two genes, bioC and bioH, whose corresponding proteins are responsible for the synthesis of Pm-CoA, have been identified. The enzymatic function of the gene products BioH and BioC is not known at present (Lemoine et al., Mol. Microbio. 19, 1996: 645–647, DeMoll, E., *Escherichia coli* and Salmonella, eds. Neidhardt, F. C. et al. ASM Press, Washington D.C., USA, 1996: 704–708, ISBN 1-55581-084-5). Pm-CoA is converted into biotin in four further enzymatic steps. Starting from Pm-CoA there is initially condensation with alanine to give 7-keto-8-aminopelargonic acid (KAPA). The gene product for this conversion is BioF (KAPA synthetase). KAPA is transaminated by BioA (DAPA aminotransferase) with the cosubstrate S-adenosylmethionine to give 7,8-diaminopelargonic acid. The next step results, after an ATP-dependent carboxylation reaction, in dethiobiotin (DTB) and is catalyzed by BioD (dethiobiotin synthase). In the last step, DTB is converted into biotin. This step is catalyzed by BioB (biotin synthase). The genes bioF, bioA, bioD, and bioB coding for the proteins-which have been described are encoded in *E. coli* on a bidirectional operon. This operon is located between the λ attachment site and the uvrB gene locus at about 17 minutes on the *E. coli* chromosome (Berlyn et al. 1996: 1715–1902). Two other genes are additionally encoded on this operon, one of which, bioc, has functions which have already been described in the synthesis of Pm-CoA, while it has not yet been possible to assign a function to an open reading frame behind bioA (WO94/8023, Otsuka et al., J. Biol. Chem. 263, 1988: 19577–85).

Highly conserved homologs to the *E. coli* proteins BioF, A, D, B have been found in B. sphaericus, *B. subtilis*, Syneccocystis sp. (Brown et al. Biotechnol. Genet. Eng. Rev. 9, 1991: 295–326, Bower et al., J. Bacteriol. 175, 1996: 4122–4130, Kaneko et al., DNA Res. 3, 3, 1996: 109–136), archaebacteria such as Methanococcus janaschi, yeasts such as Saccharomyces cerevisiae (Zhang et al., Arch. Biochem. Biophys. 309, 1, 1994: 29–35) or in plants such as *Arabidopsis thaliana* (Baldet et al., C. R. Acad. Sci. III, Sci. Vie. 319, 2, 1996: 99–106)).

The synthesis of Pm-CoA appears to take place differently in the two Gram-positive microorganisms which have been investigated to date than in *E. coli*. It has not been possible to find any homologs of bioH and bioC (Brown et al. Biotechnol. Genet. Eng. Rev. 9, 1991: 295–326).

Biotin is an optically active substance with three centers of chirality. It is currently prepared commercially only in a multistage costly chemical synthesis.

As an alternative to this chemical synthesis, many attempts have been made to set up a fermentation process for preparing biotin using microorganisms. It has been possible, by cloning the biotin operon on multi-copy plasmids, to increase biotin synthesis in microorganisms transformed with these genes. A further increase in biotin synthesis has been achieved by deregulation of biotin gene expression via selection of birA mutants (Pai C. H., J. Bacteriol. 112, 1972: 1280–1287). Combining the two approaches, ie. expression of the plasmid-encoded biosynthesis genes in a regulation-deficient strain (EP-B-0 236 429), resulted in a further increase in productivity. In this case, either the biotin operon can remain under the control of its native bidirectional promoter (EP-B-0 236 429), or its genes can be placed under the control of a promoter which can be regulated externally (WO94/8023).

It has not been possible to achieve commercially adequate productivity by previous approaches to the preparation of biotin by fermentation in *E. coli*. It has emerged that the yield in the preparation of biotin by fermentation is caused by the incomplete conversion of DTB into biotin by the BioB gene product (biotin-synthase). Cells which harbor mutations in the bioB gene are unable to grow on DTB and thus to convert DTB into biotin. The chemical and enzymatic mechanism of the conversion of DTB into biotin is at present only incompletely understood and elucidated.

Intensive genetic investigations to date have been unable to identify further proteins involved in the reaction. Characterization of the conversion of DTB into biotin has hitherto been carried out only in bacterial and plant cell extracts (WO94/8023, EP-B-0 449 724, Sanyal et al. Arch. Biochem. Biophys., Vol. 326, No. 1, 1996: 48–56 and Biochemistry 33, 1994: 3625–3631, Baldet et al. Europ. J. Biochem. 217, 1, 1993: 479–485, Méjean et al. Biochem. Biophys. Res. Commun., Vol. 217, No. 3, 1995: 1231–1237, Ohshiro et al., Biosci. Biotechnol. Biochem., 58, 9, 1994: 1738–1741).

These investigations have shown that low molecular weight factors such as S-adenosylmethionine, NADPH, cysteine, thiamine, $Fe^{2+}$, asparagine, serine, fructose 1,6-bisphosphate stimulate the synthesis of biotin (Ohshiro et al., Biosci. Biotechnol. Biochem., 58, 9, 1994: 1738–1741, Birch et al., J. Biol. Chem. 270, 32, 1995: 19158–19165, Ifuk et al., Biosci. Biotechnol. Biochem., 59, 2, 1995: 185–189). Besides these low molecular weight factors, other proteins which stimulate the synthesis of biotin from DTB in the presence of BioB have been identified. These are flavodoxin and flavodoxin-NADPH reductase (Birch et al., J. Biol. Chem. 270, 32, 1995: 19158–19165, Ifuku et al., Biosci. Biotechnol. Biochem., 59, 2, 1995: 185–189, Sanyal et al., Arch. Biochem. Biophys. 326, 1, 1996: 48–56).

The biotin synthesis and lipoic acid synthesis exhibit great homology. In both synthetic pathways there is insertion of a sulfur, or two sulfur atoms, between non-activated carbon atoms in the last stage of the synthesis. The synthesis of lipoic acid is at present only inadequately characterized (DeMoll, E., *Escherichia coli* and *Salmonella*, eds. Neidhardt, F. C. et al. ASM Press, Washington D.C., USA, 1996: 704–708, ISBN 1-55581-084-5). To date, only two necessary genes have been identified in *E.coli*: lipA and lipB. Both genes are located in an operon, with an as yet uncharacterized open reading frame (=ORF) between the two genes. Another gene lplA is able to transfer lipoic acid via a lipoyl-AMP intermediate to lysine. This reaction is thus similar to the activity of birA. Homologous regions in the amino acid sequence have been identified by sequence comparisons between LipA and BioB. These include, inter alia, a cysteine cluster. It has been shown that LipA catalyzes the incorporation of two sulfur atoms into the lipoic acid (DeMoll, E., *Escherichia coli* and *Salmonella*, eds. Neidhardt, F. C. et al. ASM Press, Washington D.C., USA, 1996: 704–708, ISBN 1-55581-084-5).

The results concerning the origin of the sulfur in the biotin molecule are contradictory. Investigations on biotin synthesis in whole cell extracts showed that radioactivity was incorporated into biotin in the presence of $^{35}$S-labeled cysteine; sulfur incorporation into the biotin molecule was undetectable either with $^{35}$S-labeled methionine or with S-adenosylmethionine (Ifuku et al., Biosci. Biotechnol. Biochem. 59, 2, 1995: 184–189, Birch et al., J. Biol. Chem.270, 32, 1995: 19158–19165).

This contrasts with investigations on purified BioB protein in the presence of $^{35}$S-labeled cysteine and without addition of cell extracts, in which case although biotin synthesis was observed there was no incorporation of radioactivity into the biotin molecule (Sanyal et al., Arch. Biochem. Biophys. 326, 1, 1996: 48–56, Méjean et al., Biochem. Biophys. Res. Commun. 2127, 3, 1995: 1231–1237). Under these synthesis conditions, without addition of cell extract, the amount of biotin formed was small and corresponded to a maximum of about 2 mol of biotin/mol of BioB (Sanyal et al., Arch. Biochem. Biophys. 326, 1, 1996: 48–56) or 0.1 mol of biotin/mol of BioB (Méjean et al., Biochem. Biophys. Res. Commun. 2127, 3, 1995: 1231–1237). According to these investigations, sulfur can be incorporated into biotin without using cysteine as sulfur donor. This biotin formation without an external source of sulfur might be explained by a transfer of sulfur from the 2Fe-2S cluster which has been detected in BioB. The actual source of sulfur for biotin synthesis is still unclear. It has thus not yet been possible to demonstrate a genuine catalytic activity of BioB in vitro.

Despite this large number of approaches, the yield of biotin from microbial fermentation is currently insufficient for industrial production.

DETAILED DESCRIPTION OF THE INVENTION

Figure 1:
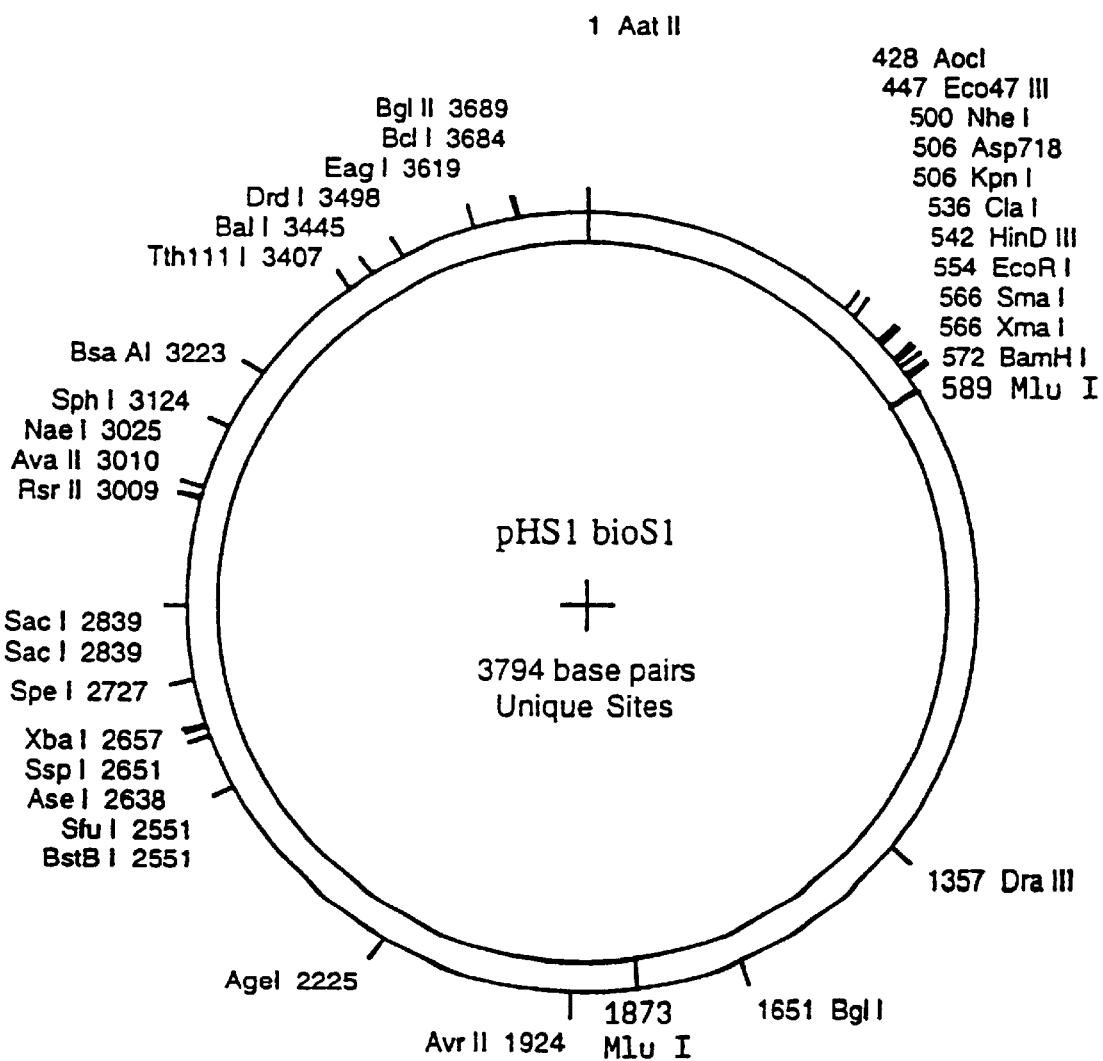
FIG. 1 is a pictorial depiction of the construct pHS1 bioS1. (SEQ ID No. 5)

It is an object of the present invention to develop an industrial process for preparing biotin by fermentation which optimizes as far as possible the conversion of dethiobiotin into biotin, and thus makes improved biotin synthesis possible.

We have found that this object is achieved by the novel process for preparing biotin which comprises expressing a biotin gene having the sequence SEQ ID No. 1 or SEQ ID No. 3, and its functional variants, analogs or derivatives, in a prokaryotic or eukaryotic host organism able to synthesize biotin, cultivating this organism and using the synthesized biotin directly, after removal of the biomass or after purification of the biotin.

The biotin genes used in the novel process and having the sequences SEQ ID No. 1 and SEQ ID No. 3, respectively, are kept in the SwissProt databank under accession numbers AE000364 and D90811. The sequence D90811 has additionally been described by Aiba et al. in DNA Res. 3, 6, 1996: 363–377. Homology with the NifS protein has been noted for both sequences in the databank. Further information on these sequences is not available from the databank or the publication.

The productivity of biotin synthesis can be markedly increased by expressing the sequences SEQ ID No. 1 and/or SEQ ID No. 3 in a prokaryotic or eukaryotic host organism. Expression of the genes increases the synthesis of biotin from dethiobiotin by a factor of at least 2 by comparison with the control without these genes, preferably by a factor of more than 3. The sequence SEQ ID No. 1 is preferably used.

After isolation and sequencing it is possible to obtain the biotin genes which are used in the novel process, have the nucleotide sequences SEQ ID No. 1 and SEQ ID No. 3, and code for the amino acid sequences indicated in SEQ ID No: 2 and SEQ ID No. 4, or their allelic variants. Allelic, variants mean variants of SEQ ID No. 1 or SEQ ID No. 3 displaying from 40 to 100% homology at the amino acid level, preferably from 50 to 100%, very particularly preferably from 80 to 100%. Allelic variants comprise, in particular, functional variants obtainable by deletion, insertion or substitution of nucleotides from the sequence depicted in SEQ ID No: 1 or SEQ ID No: 3, where the enzymatic activity is, however, retained.

Analogs of SEQ ID No: 1 or SEQ ID No: 3 mean, for example, their bacterial, fungal, plant or yeast homologs, truncated sequences, single-stranded DNA or RNA of the coding and noncoding DNA sequence.

Derivatives mean, for example, promoter variants. The promoters which precede the stated nucleotide sequences can be altered by one or more nucleotide exchanges, by insertion(s) and/or deletion(s) without, however, adversely affecting the functionality or activity of the promoters. The promoters can furthermore have their activity increased by altering their sequence, or be replaced completely by more effective promoters, even from heterologous organisms.

Derivatives also mean variants whose nucleotide sequence has been altered in the region from −1 to −30 in front of the start codon in such a way that gene expression and/or protein expression is increased. This is advantageously effected by altering the Shine-Dalgarno sequence.

Suitable prokaryotic host organisms in the novel process are, in principle, all biotin-synthesized Gram-negative or Gram-positive bacteria. Examples which may be mentioned of Gram-negative bacteria are Enterobacteriaceae such as the genera Escherichia, Aerobacter, Enterobacter, Citrobacter, Shigella, Klebsiella, Serratia, Erwinia or Salmonella, Pseudomonadaceae such as the genera Pseudomonas, Xanthomonas, Burkholderia, Gluconobacter, Nitrosomonas, Nitrobacter, Methanomonas, Comamonas, Cellulomonas or Acetobacter, Azotobacteraceae such as the genera Azotobacter, Azomonas, Beijerinckia or Derxia, Neisseriaceae such as the genera Moraxella, Acinetobacter, Kingella, Neisseria or Branhamella, the Rhizobiaceae such as the genera Rhizobium or Agrobacterium or the Gram-negative genera Zymomonas, Chromobacterium or Flavobacterium. Examples of Gram-positive bacteria which may be mentioned are the endospore-forming Gram-positive aerobic or anaerobic bacteria such as the genera Bacillus, Sporolactobacillus or Clostridium, the coryneform bacteria such as the genera Arthrobacter, Cellulomonas, Curtobacterium, Corynebacterium, Brevibacterium, Microbacterium or Kurthia, the Actinomycetales such as the genera Mycobacterium, Rhodococcus, Streptomyces or Nocardia, the Lactobacillaceae such as the genera Lactobacillus or Lactococcus, the Gram-positive cocci such as the genera Micrococcus or Staphylococcus.

Bacteria preferably used in the novel process are of the genera Escherichia, Citrobacter, Serratia, Klebsiella, Salmonella, Pseudomonas, Comamonas, Acinetobacter, Azotobacter, Chromobacterium, Bacillus, Clostridium, Arthrobacter, Corynebacterium, Brevibacterium, Lactococcus, Lactobacillus, Streptomyces, Rhizobium, Agrobacterium or Staphylococcus. Particularly preferred genera and species are *Escherichia coli, Citrobacter freundii, Serratia marcescens, Salmonella typhimurium, Pseudomonas mendocina, Pseudomonas aeruginosa, Pseudomonas mutabilis, Pseudomonas chlororaphis, Pseudomonas fluorescens, Comamonas acidovorans, Comamonas testosteroni, Acinetobacter calcoaceticus, Azotobacter vinelandii, Chromobacterium violaceum, Bacillus subtilis, Bacillus sphaericus, Bacillus stearothermophilus, Bacillus pumilus, Bacillus licheniformis, Bacillus amyloliquefaciens, Bacillus megaterium, Bacillus cereus, Bacillus thuringiensis, Arthrobacter citreus, Arthrobacter paraffineus, Corynebacterium glutamicum, Corynebacterium primorioxydans*, Corynebacterium sp., *Brevibacterium ketoglutamicum, Brevibacterium linens*, Brevibacterium sp., *Streptomyces lividans, Rhizobium leguminosarum* or *Agrobacterium tumefaciens*. Bacteria which already have increased natural biotin production are advantageously used.

The taxonomic positioning of the stated genera has been subject to great change in recent years and is still in a state of flux because incorrect genus and species names are being corrected. This frequent need in the past for taxonomic regrouping of said genera within the classification of bacteria means that families, genera and species other than those mentioned above are also suitable for the novel process.

Suitable eukaryotic host organisms for the novel process are, in principle, all biotin-synthesizing organisms such as fungi, yeasts, plants or plant cells. Yeasts which may be mentioned as preferred are the genera Rhodotorula, Yarrowia, Sporobolomyces, Saccharomyces or Schizosaccharomyces. Particularly preferred genera and species are *Rhodotorula rubra, Rhodotorula glutinis, Rhodotorula graminis, Yarrowia lipolytica, Sporobolomyces salmonicolor, Sporobolomyces shibatanus* or *Saccharomyces cerevisiae*.

It is possible in principle to use all plants as host organism, and preferred plants are those important in livestock feeding or human nutrition, such as corn, wheat, barley, rye, potatoes, peas, beans, sunflowers, palms, millet, sesame, copra or oilseed rape. Plants such as *Arabidopsis thaliana* or *Lavendula vera* are also suitable. Plant cell cultures, protoplasts from plants or callus cultures are particularly preferred.

It is advantageous to use in the novel process microorganisms such as bacteria, fungi, yeasts or plant cells which are able to secrete biotin into the culture medium and which, where appropriate, additionally have increased natural biotin synthesis. It is also possible and advantageous for these organisms to be defective in respect of the regulation of their biotin biosynthesis, ie. there is no, or only very diminished, regulation of the synthesis. This regulation defect results in these organisms having a considerably higher biotin productivity. A regulation defect of this type is known, for example, for *Escherichia coli* as the birA defective mutant and ought preferably to be present in the cells in the form of a defect which can be inducted by external influences, for example is temperature-inducible. Organisms which do not naturally produce biotin can also be used in principle after they have been transformed with the biotin genes.

In order to increase the overall biotin productivity further, the organisms in the novel process advantageously ought additionally to comprise at least one other biotin gene selected from the group of bioA, bioB, bioF, bioC, bioD, bioH, biop, biow, bioX, bioy or bioR. This additional gene or these additional genes may be present in one or more copies in the cell. They may be located on the same vector as the sequences SEQ ID No. 1 and/or SEQ ID No. 3, or have been integrated on separate vectors or else into the chromosome. The sequences SEQ ID No. 1 and/or SEQ ID No. 3 can also be inserted into the genome.

The novel gene construct means the biotin gene sequences SEQ ID No. 1 and SEQ ID No. 3 and their functional variants, analogs or derivatives, which are functionally linked to one or more regulatory signals to increase gene expression. In addition to these novel regulatory sequences, the natural regulation of these sequences in front of the actual structural genes may still be present and, where appropriate, have been genetically modified so that the natural regulation has been switched off and the expression of the genes has been increased. However, the gene construct may also have a simpler structure, ie. no additional regulatory signals have been inserted in front of the sequences SEQ ID No. 1 and/or SEQ ID No. 3, and the natural promoter with its regulation has not been deleted. Instead, the natural regulatory sequences have been mutated in such a way that there is no longer any regulation by biotin, and gene expression is increased. It is also possible to insert additional, advantageous regulatory elements at the 3' end of the DNA sequences. The biotin genes having sequences SEQ ID No. 1 and/or SEQ ID No. 3 may be present in one or more copies in the gene construct.

Advantageous regulatory sequences for the novel process are, for example, present in promoters such as cos, tac, trp, tet, trp-tet, lpp, lac, lpp-lac, lacI$^{q-}$, T7, T5, T3, gal, trc, ara, SP6, $\lambda$-P$_R$ or the $\lambda$-P$_L$ promoter, which are advantageously used in Gram-negative bacteria. Further advantageous regulatory sequences are, for example, present in the Gram-positive promoters amy and SPO2, in the yeast promoters ADC1, MF$\alpha$, AC, P-60, CYC1, GAPDH or in the plant promoters CaMV/35S, SSU, OCS, lib4, usp, STLS1, B33, nos or in the ubiquitin or phaseolin promoter.

It is possible in principle for all natural promoters with their regulatory sequences like those mentioned above to be used for the novel process. It is furthermore possible and advantageous to use synthetic promoters.

The gene construct may comprise further biotin genes selected from the group of bioA, bioB, bioF, bioC, bioD, bioH, biop, biow, bioX, bioy or bioR in one or more copies, each of which may have its own promoter or else may be under the control of the promoter of sequences SEQ ID No. 1 or SEQ ID No. 3.

The gene construct is, for expression in the abovementioned host organism, advantageously inserted into a host-specific vector which makes optimal expression of the genes in the host possible. Examples of suitable vectors in *E. coli* are pLG338, pACYC184, pBR322, pUC18, pUC19, pKC30, pRep4, pHS1, pHS2, pPLc236, pMBL24, pLG200, pUR290, pIN-III$^{113}$-B1, λgt11 or pBdCI, in Streptomyces are pIJ101, pIJ364, pIJ702 or pIJ361, in Bacillus are pUB110, pC194 or pBD214, in Corynebacterium are pSA77 or pAJ667, in fungi are PALS1, pIL2 or pBB116, in yeasts are YEp6, YEpl3 or pEMBLYe23 or in plants are pLGV23, pGHlac$^+$, pBIN19, pAK2004 or pDH51. Said vectors represent a small selection from the possible vectors. Further vectors are well-known to the skilled worker and can be found, for example, in the book Cloning Vectors (Eds. Pouwels P. H. et al. Elsevier, Amsterdam-New York-Oxford, 1985, ISBN 0 444 904018).

Expression systems mean the combination of the host organisms mentioned above by way of example and the vectors suiting the organisms, such as plasmids, viruses or phages, such as the T7 RNA polymerase/promoter system or vectors with regulatory sequences for phage λ.

The term expression systems preferably means the combination of *Escherichia coli* and its plasmids and phages and the relevant promoters, and Bacillus and its plasmids and promoters.

Also suitable for advantageous novel expression of SEQ ID No. 1 and SEQ ID No. 3 are other 3' and/or 5' terminal regulatory sequences.

These regulatory sequences are intended to make specific expression of the biotin genes and protein expression possible.

This may mean, for example, depending on the host organism that the gene is expressed or overexpressed only after induction, or that it is immediately expressed and/or overexpressed.

The regulatory sequences and factors may moreover preferably have a beneficial effect on, and thus increase, biotin gene expression. Thus, it is possible and advantageous to enhance the regulatory elements at the level of transcription by using strong transcription signals such as promoters and/or "enhancers". However, it is also possible besides this to enhance translation by, for example, improving the stability of the mRNA.

"Enhancers" mean, for example, DNA sequences which bring about, is via an improved interaction between RNA polymerase and DNA, an increase in biotin gene expression.

An accentuation of the proteins derived from sequences SEQ ID No. 1 or SEQ ID No. 3 and their enzyme activity can be achieved, for example by comparison with the initial enzymes, by modifying the corresponding gene sequences or the sequences of its homologs by classical mutagenesis such as UV irradiation or treatment with chemical mutagens and/or by specific mutagenesis such as site-directed mutagenesis, deletion(s), insertion(s) and/or substitution(s). Increased enzyme activity can also be achieved, besides the gene amplification described, by eliminating factors which repress enzyme biosynthesis and/or by synthesizing active, not inactive, enzymes.

The novel process advantageously increases the conversion of DTB into biotin and thus the biotin productivity overall via the biotin genes having the sequences SEQ ID No. 1 or SEQ ID No. 3 which have been cloned into the organisms via vectors and/or into the chromosome.

In the novel process, the microorganisms comprising SEQ ID No. 1 and/or SEQ ID No. 3 are cultured in a medium which allows these organisms to grow. This medium may be a synthetic or a natural medium. Media known to the skilled worker and depending on the organism are used. The media used for growing the microorganisms comprise a source of carbon, a source of nitrogen, inorganic salts and, where appropriate, small amounts of vitamins and trace elements.

Examples of advantageous sources of carbon are sugars such as mono-, di- or polysaccharides such as glucose, fructose, mannose, xylose, galactose, ribose, sorbose, ribulose, lactose, maltose, sucrose, raffinose, starch or cellulose, complex sources of sugars, such as molasses, sugar phosphates such as fructose 1,6-bisphosphate, sugar alcohols such as mannitol, polyols such as glycerol, alcohols such as methanol or ethanol, carboxylic acids such as citric acid, lactic acid or acetic acid, fats such as soybean oil or rapeseed oil, amino acids such as glutamic acid or aspartic acid, or amino sugars, which can also be used as source of nitrogen.

Advantageous sources of nitrogen are organic or inorganic nitrogen compounds or materials which contain these compounds. Examples are ammonium salts such as $NH_4Cl$ or $(NH_4)_2SO_4$, nitrates, urea or complex sources of nitrogen, such as corn steep liquor, brewer's yeast autolysate, soybean flour, wheat gluten, yeast extract, meat extract, casein hydrolysate, yeast or potato protein, which may often also serve as source of nitrogen.

Examples of inorganic salts are the salts of calcium, magnesium, sodium, manganese, potassium, zinc, copper and iron. The anion in these salts which should be particularly mentioned is the chloride, sulfate and phosphate ion. An important factor in enhancing the productivity in the novel process is the addition of $Fe^{2+}$ or $Fe^{3+}$ salts and/or potassium salts to the production medium.

Other growth factors are added to the nutrient medium where appropriate, such as vitamins or growth promoters such as riboflavin, thiamine, folic acid, nicotinic acid, pantothenate or pyridoxine, amino acids such as alanine, cysteine, asparagine, aspartic acid, glutamine, serine, methionine or lysine, carboxylic acids such as citric acid, formic acid, pimelic acid or lactic acid, or substances such as dithiothreitol.

It is possible, where appropriate, to add antibiotics to the medium to stabilize the vectors with the biotin genes in the cells.

The mixing ratio of said nutrients depends on the mode of fermentation and is established in the individual case. It is possible for the medium components all to be present at the start of the fermentation after they have been, if necessary, sterilized separately or sterilized together, or else to be added during the fermentation as required.

The cultivation conditions are established so that the organisms grow optimally and so that the best possible yields are obtained. Preferred cultivation temperatures are from 15° C. to 40° C.

Temperatures from 25° C. to 37° C. are particularly advantageous. The pH is preferably kept in a range from 3 to 9. The pH is particularly advantageously from 5 to 8. An incubation time of from 8 to 240 hours, preferably from 8 to 120 hours, is generally sufficient. During this time, the maximum amount of biotin accumulates in the medium and/or is available after disruption of the cells.

The novel process for preparing biotin can be carried out continuously or batchwise. If whole plants are regenerated from the plant cells transformed with the biotin genes, these plants can be grown and propagated quite normally in accordance with the novel process.

EXAMPLE

Based on the consideration that the conversion of DTB into biotin might involve, apart from BioB and the other known cofactors, possibly an Fe-S cluster-regenerating enzyme, an attempt was made to identify and clone such a hypothetical gene.

NifS genes are able to regenerate sulfur atoms in an Fe-S cluster of proteins involved in nitrogen fixation (Zheng et al., Proc. Natl. Acad. Sci. USA 90, 1993: 2754–2758 and Biochemistry 33, 1994: 4714–4720). It was possible by comparing all known proteins of the NifS class in the Swiss-Prot and PIR databanks using the Lasergene program package (DNA-Star Inc.) in the megalign mode to identify a strictly conserved region of these proteins having the amino acid sequence HK(I,L)xGPxG (x corresponds to amino acids whose conservation is low or not retained). The fact that there is complete conservation of this sequence indicates that these amino acids (=Aa) are important in the functioning of these proteins. These conserved amino acids are referred to as motif I hereinafter.

The Aa motif described in this way was used as comparison sequence for further analysis of the Swiss-Prot/PIR release 93 or 94 databank to search for proteins or ORFs (=open reading frames) in which this NifS functional sequence is completely conserved. The program employed for the sequence analysis was the Geneman program from the DNA-Star package. The analysis parameters were fixed as follows: consensus sequence menu with 80% conservation of the motif.

This search resulted in the finding that, besides proteins which have already been identified as NifS-homologous proteins, there are other proteins or ORFs which have this sequence motif. Among the other sequences present in the databank, it was possible to identify an open reading frame from *E. coli* which has significant conservation of the consensus sequence and is, as our studies have shown, involved in biotin synthesis. This open reading frame, which is referred to as ECU29581_24 (=SEQ ID No. 1=ORF401), codes for a hypothetical protein of 401 Aa which is derived from this sequence. It emerged that this sequence had been sequenced as part of the *E. coli* genome sequencing by F. Blattner and co-workers (DNA-Research 1996), without its function having been recognized. This sequence (SEQ ID No. 1) is referred to as BioS1 hereinafter.

Comparison of the protein sequence of BioS1 with that of NifS from A. vinelandii (program: DNA-Star "megalign" in mode: pairwise Lipman-Pearson alignment, analysis parameters: k-tuple 2, gap penalty 4, gap length penalty 12) shows that ECU29581_24 also has a homology of 27.6% with NifS from A. vinelandii in other regions of the sequence over a range of 218 Aa. The homology with the protein identified as NifS from Rhodococcus capsulatus is 25.3% over a range of 376 Aa.

It was possible to identify further sequences having homologies with ECU29581_24 in the SwissProt/PIR databank (Geneman program/sequence similarity mode; default settings). The greatest similarity found to the ECU29581_24 sequence is shown by a translated ORF (=open reading frame) from H. influenzae (databank name HIU00082_62). A sequence homology of 45.5% was found for BioS1 and HIU00082_62 over the entire length of the two proteins. The sequence similarity or the homology of the two proteins is thus significantly greater than between ECU29581_24 (=BioS1) and NifS from R. capsulatus or A. vinelandii. The protein is thus presumably the H. influenzae homolog to BioS1.

Fleischmann et al. (Science. 269, 1995: 496–512) found not only ORF HIU00082_62 but also another ORF (HIU00072_10) in H. influenzae on the basis of its similarity to the NifS sequence.

It was concluded on the basis of this description by Fleischmann et al. that another NifS-like gene, besides bioS1, also exists in *E. coli*. This hypothetical gene has been called bioS2.

1. Construction of the Vectors pHS1 and pHS2:

The plasmids pHS1 and pHS2 consist of various cassettes which carry an origin of replication, a resistance cassette, a promoter, a cloning site and terminators. The plasmids were assembled from various DNA fragments. The DNA fragments necessary for this were prepared by PCRs with various plasmids as templates.

a.) Preparation of the Cassette with an Origin of Replication:

In order to provide the origin of replication from a P15A replicon-containing plasmid as clonable cassette, a DNA fragment with a length of 919 bases was isolated from the plasmid by a PCR with the plasmid pRep4 (Quiagen) with the oligonucleotides P15A,1 (5'-GGCCCCTAGGGGATATATTCCGCTTCCTCGC-3') (SEQ ID NO:13) and P15A,2 (5'-GGCCACTAGTAACAACTTATATCGTATGGGG-3') (SEQ ID NO:14). The fragment was cut with the restriction enzymes AvrII and SpeI in a suitable buffer.

PCR Conditions:

2.5 U of Taq polymerase and 15 pmol of the oligonucleotides were used in 100 μl of solution to isolate the replication cassette from the plasmid pRep4. The oligonucleotides were annealed at 50° C. Elongation took place at 72° C. for 1 min over 30 cycles.

b.) Preparation of the Kanamycin Resistance Cassette:

In order to provide a kanamycin-resistance cassette as clonable cassette, a DNA fragment with a length of 952 bases was isolated by a PCR from a plasmid containing the kanamycin-resistance cassette (pRep4, Quiagen) with the oligonucleotides Kan-R,1 (5'-GGCCGAGCTCTCGAACCCCAGAGTCCCGCT-3') (SEQ ID NO:15) and Kan-R,2 (5'-GGCCGACGTCGGAATTGCCAGCTGGGGCGC-3') (SEQ ID NO:16). The fragment was cut with AatII and SacI in a suitable buffer.

PCR Conditions:

2.5 U of Taq polymerase and 15 pmol of the oligonucleotides were used in 100 μl of solution to isolate the kanamycin resistance cassette from the plasmid pRep4. The oligonucleotides were annealed at 50° C. Elongation took place at 72° C. for 1 min over 30 cycles.

c.) Preparation of the Termination Regions:

In order to provide the terminator T0 from phage lambda as clonable cassette, a DNA fragment with a length of 120 bases was isolated by a PCR with the plasmid pDS12-luzi (Schroder H. et al., EMBO Journal. 12, 11, 1993: 4137–4144) as template with the oligonucleotides T0,1 (5'-GGCCGAGCTCGCTTGGACTCCTGTTGATAG-3') (SEQ ID NO:17) and T0,2 (5'-GGCCACTAGTGCTTGGATTCTCACCAATAAA AAACGCCC-3') (SEQ ID NO:18). The fragment was cut by the enzymes SpeI and SacI in a suitable buffer.

Template for T0: pDS12-luzi 2.5 U of Taq polymerase and 15 pmol of the oligonucleotides were used in 100 μl of solution to isolate the termination region from the plasmid pDS12-luzi. The oligonucleotides were annealed at 50° C. Elongation took place at 72° C. for 0.5 min over 30 cycles. Then a fragment 120 bp in size was isolated and purified. This fragment was digested with 20 U each of SpeI and SacI.

In order to provide the terminator T1 from the rrnB operon as clonable cassette, a DNA fragment with a length of 120 bp was isolated by a PCR with the plasmid pDS12-luzi (Schroder et al., see above) as template and with the aid of the oligonucleotides T1,1 (5'-GGCCCCTAGGTCTAGGGCGGCGGATTTGTCC-3') (SEQ ID NO:19) and T1,2 (5'-GGCCTCTAGAGGCATCAAATAAAACGAAAGGC-3') (SEQ ID NO:20). The fragment was cut by the enzymes XbaI and AvrII in a suitable buffer.

Template for T1: pDS12-luzi 2.5 U of Taq polymerase and 15 pmol of the oligonucleotides were used in 100 μl of solution to isolate the termination region from the plasmid pDS12-luzi. The oligonucleotides were annealed at 50° C. Elongation took place at 72° C. for 0.5 min over 30 cycles. Then a fragment 120 bp in size was isolated and purified. This fragment was digested with 20 U each of XbaI and AvrII.

d.) Preparation of the Promoters for pHS1 and pHS2:

The oligonucleotides PPHS1,1 (5'-TCGAGATAGCATTTTTATCCATAAGATT-AGCCGATCCTAAGGTTTACAATTGTGAGCGCTC CAATTATGATAGATTCAATTGTGAGCGGATAAC AATTTCACACACGCTAGCGGTAC-3') (SEQ ID NO:21) and PPHS1,2 (5'-CGCTAGCGTGTGTGAAATTGTTATC-CGCTCACAATTGAATCTATCATAATTGTGAGCGCTC ACAATTGTAAACCTTAGGATCGGCTAATCTTATG GATAAAAATGCTATC-3') (SEQ ID NO:22) and PPHS2,1 (5'-AATTCTCCCTATCAGTGATAGAGATTGA-CATCCCTATCAGTGATAGAGATACTGAGACATC ACCAGGACGCACTGACCG-3') (SEQ ID NO:23) and PPHS2,2 (5'-AATTCGGTCAGTGCGTCCTGGTGAT-GTCTCAGTATCTCTATCACTGATAGGGATGTCAATC TCTATCACTGATAGGGAGG-3') (SEQ ID NO:24) were prepared by chemical synthesis. The oligonucleotides PPHS1,1 and PPHS1,2 and PPHS2,1 and PPHS2,2, were respectively mixed in a concentration of 1 μg/μl, incubated at 95° C. for 5 min and then cooled slowly. The annealed oligonucleotides were employed in a concentration of 10 ng/μl in the ligation. Oligonucleotides PPHS1,1 and PPHS1,2 formed the promoter for the plasmid pHS1, and oligonucleotides PPHS2,1 and PPHS2,2 formed that for the plasmid pHS2.

e.) Preparation of the Cloning Site:

To construct the cloning site, the two oligonucleotides PMCS1,1 (5'-GTACCGGGCCCCCCCTCGAGGTCGACGG-TATCGATAAGCTTGATATCGAATTCCTGCAGCC CGGGGGATCCCATGGTA-3') (SEQ ID NO:25) and PMCS1,2 (5'-ACGCGTACCATGGGATCCCCCGGGCTG-CAGGAATTCGATATCAAGCTTATCGATACCGTCG ACCTCGAGGGGGGGCCCGGTACC-3') (SEQ ID NO:26) were synthesized. The two oligonucleotides were mixed in a concentration of 1 μg/μl, incubated at 95° C. for 5 min and then cooled slowly. The annealed oligonucleotides were employed in a concentration of 10 ng/μl in the ligation.

f.) Procedure for Cloning pHS1 and pHS2

Starting from pDS12 luci, the ampR cassette of the plasmid was cut out by SacI/AatII digestion and replaced by a corresponding SacI/AatII fragment which contains the kanamycin resistance cassette. The vector obtained after transformation and isolation of positive clones underwent SpeI/SacI digestion, and the PCR-amplified terminator T0 was inserted as SpeI/SacI fragment downstream of the kanamycin resistance cassette. The vector obtained after transformation and isolation of positive clones was digested with XbaI/AvrII, and the PCR-amplified terminator T1 was inserted as xbaI/AvrII fragment. The resulting vector was digested with XhoI/EcoRI and ligated to the respectively annealed promoter oligonucleotides (PPHS1,1 and PPHS1,2, and PPHS2,1 and PPHS2,2). The resulting vector underwent XbaI digestion and was filled in using the Klenow fragment and then, after KpnI digestion, the vector band without the luziferase fragment was isolated. Two further annealed oligonucleotides (PMCS1,1 PMCS1,2) which contain the cloning site were ligated to the vectors digested in this way.

2. Cloning of bioS1 (ECU29581_24, SEQ ID No. 1):

The gene which codes for BioS1 was amplified from the chromosome of $E.\ coli$ by a PCR, provided with optimized translation signals, and cloned into a vector which makes overexpression of the gene in $E.\ coli$ strains possible.

a.) Development of Oligonucleotides for Amplifying the bioS1 Gene from the $E.\ coli$ Chromosome:

BioS1 is to be amplified as expression cassette consisting of a ribosome binding site, the start codon of the coding sequence and the stop codon between two recognition sites for restriction enzymes. The MluI recognition sequence was chosen for both restriction cleavage sites. The bioS1 gene was cloned with the aid of the oligonucleotides PbioS1,1 (5,-CGCACGCGTGAGGAGTACCATGAACGT-3') (SEQ ID NO:27) and PbioS1,2 (5'-CGCACGCGTTTAATCCACCAATAATT-3') (SEQ ID NO:28).

PCR Procedure:
Conditions:

0,5 μg of chromosomal DNA from $E.\ coli$ W3110 was used as template. The oligonucleotides PbioS1,1 and PbioS1,2 were each employed in a concentration of 15 pM. The concentration of dNTPs was 200 μM. 2.5 U of Pwo DNA polymerase (Boehringer Mannheim) in the manufacturer's reaction buffer were used as polymerase. The volume for the PCR was 100 μl.

Amplification Conditions:

The DNA was denatured at 94° C. for 2 min. The oligonucleotides were then annealed at 55° C. for 30 sec. Elongation took place at 72° C. for 45 sec. The PCR was carried over 30 cycles.

The resulting DNA product with a size of 1200 bp was purified and digested by MluI in a suitable buffer.

Figure 2:
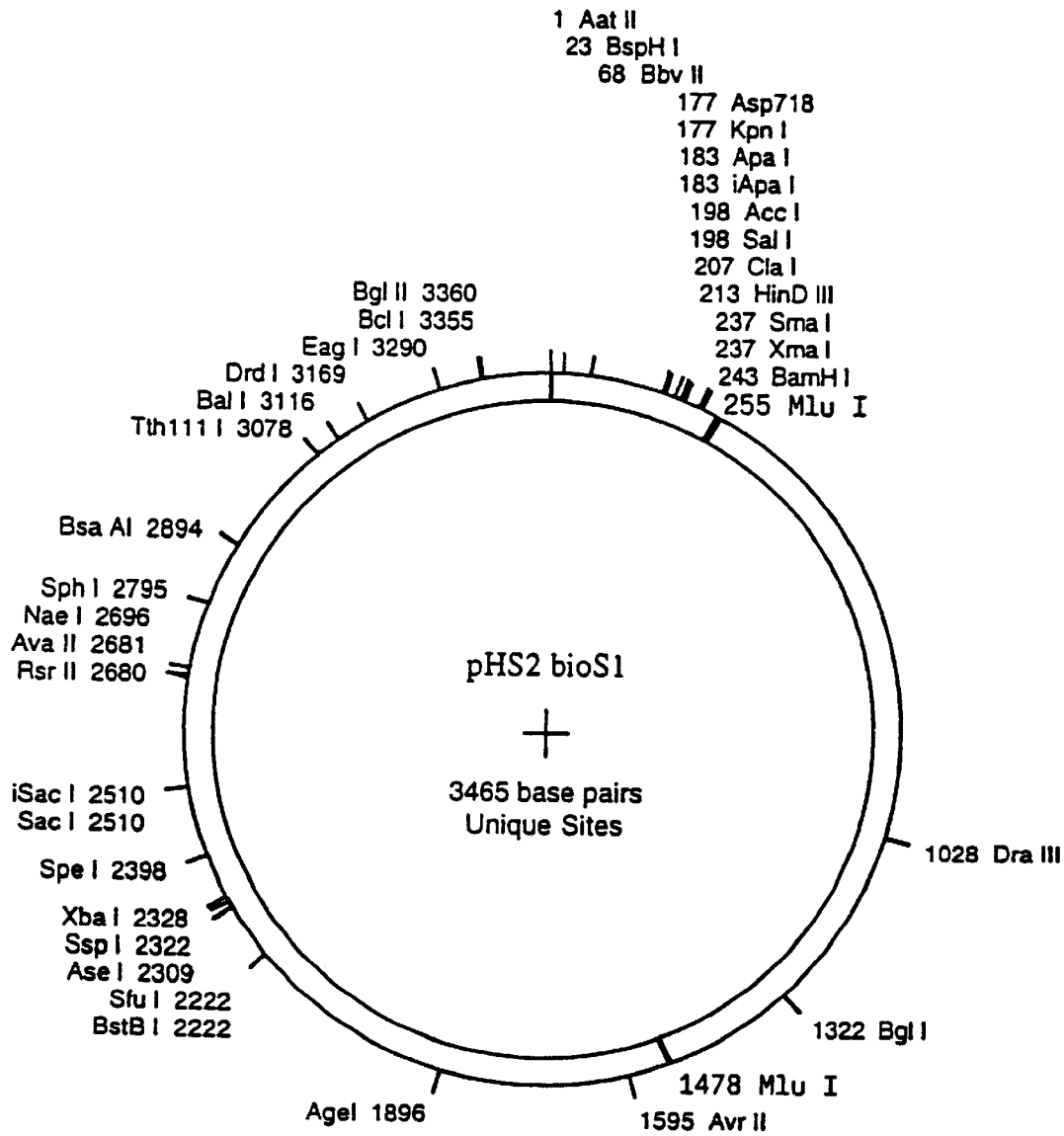
FIG. 2 is a pictorial depiction of the construct pHS2 bioS1. (SEQ ID No. 9)

5 μg of the vector pHS1 were digested by MluI and dephosphorylated by shrimp alkaline phosphatase (SAP) (Boehringer Mannheim). After denaturation of the SAP, the vector and fragment were ligated in a molar ratio of 1:3 by the rapid DNA ligation kit in accordance with the manufacturer's instructions. The ligation mixture was transformed into the strain $E.\ coli$ XL1-blue. Positive clones were identified by plasmid preparation and restriction analysis. The correct orientation of the bioS1 fragment in pHS1 was determined by restriction digestion and sequencing. The resulting construct was called pHS1 bioS1 (FIG. 1). The sequence of pHS1 bioS1 is to be found in SEQ ID No. 5. The derived amino acid sequence of bioS1 in the vector is to be found in SEQ ID No. 6. 2 µg of the vector pHS1 bioS1 were digested with MluI, and the gene bioS1 was isolated by an agarose gel. The vector pHS2 was digested with MluI, dephosphorylated with SAP and attached to the fragment bioS1 in a joint ligation. The ligation mixture was transformed into XL1-blue, and positive clones in the correct orientation were identified by plasmid isolation and restriction digestion. The resulting vector was called pHS2 bioS1 (FIG. 2). The sequence of pHS2 bioS1 is to be found in SEQ ID No. 9. The derived amino acid sequence of bioS1 in the vector is to be found in SEQ ID No. 10.

3. Cloning of bioS2 (SEQ ID No. 3):

The way of cloning into *E. coli* further genes which code for gene products which are involved in the assembly of Fe-S clusters was as follows:

A sequence comparison (Megalign program, Clustal mode) of Aa sequences of proteins in the SwissProt/PIR databank with high homology (>40%) with the NifS protein from A. vinelandii showed that, besides the sequence motif I which has been described above, the N terminus of these proteins also shows significant conservation. The Aa sequence MIYLDNXATT (SEQ ID NO:29) was identified as a typical N-terminal conserved sequence of proteins of the NifS family and was called motif II a.

Analysis of the SwissProt/PIR databank for more than 80% conservation of this sequence showed another protein in *E. coli*. 11 Aa in the N-terminal sequence of this protein are known from Edman degradation (databank name: UP06_*Ecoli*). This protein was regarded as hypothetical NifS homolog and is referred to as BioS2, in analogy to BioS1, hereinafter.

The way of cloning and sequencing the gene for the protein BioS2 was as follows. Starting from the protein sequence HIU00072_10, on the one hand the conserved amino acid motif I, and on the other hand the abovementioned Aa sequence of UP06_*Ecoli*, were used to prepare degenerate oligonucleotides which are able to amplify a fragment of the bioS2 gene. For this purpose, the two Aa motifs HIU00072_10 (motif I) and UP06_*Ecoli* (motif II b, MKLPIYLDYSAT (SEQ ID NO:30)) were reverse translated into the corresponding DNA sequences. In this way, the degenerate oligonucleotide PbioS2,1 (5'-ATGAARYTNCCNATHTAYYTNGAYTAYWSNGCNAC-3') (SEQ ID NO:31) was synthesized from motif II, and the degenerate oligonucleotide PbioS2,2 (5'-cccaghggrccrtgcagyttrtgrccrga-3') (SEQ ID NO:32) was synthesized from motif I.

PCR Procedure:

Chromosomal DNA from *E. coli* W3110 was used as template. 0.5 µg each of the oligonucleotides PbioS2,1 and PbioS2,2 were reacted in each case with 15 pmol of nucleotide mix, 2.5 U of Pwo DNA polymerase (Boehringer Mannheim) in the manufacturer's reaction buffer. The volume for the PCR was 100 µl.

Amplification Conditions:

Denaturation took place at 94° C. for 2 min. Annealing of the oligonucleotides was carried out at 45° C., and elongation was carried out at 72° C. for 45 sec. The PCR was carried out over 30 cycles. It was possible by the PCR to amplify three fragments selectively, and one of them had the size of 600 bp expected from the sequence comparisons. This DNA fragment was isolated by agarose gel purification and sequenced with the oligonucleotide PbioS2,2. The resulting DNA sequence was translated in all six possible reading frames. The resulting translated Aa sequences were then compared with the translated Aa sequence of HIU00072_10 and NifS from A. vinelandii. One of the translated reading frames shows high homology with the Aa sequence of the described ORF HIU00072_10 an d is called bioS2.

The way of determining and cloning the complete DNA sequence of bioS2 (=SEQ ID No. 3) was as follows:

Firstly, a labeled DNA probe homologous with bioS2 was prepared. This took place using the PCR-DIG labeling kit (Boehringer Mannheim). The template used for preparing the DIG-DNA probe was the described PCR product which was prepared by the oligonucleotides PbioS2,1 and PbioS2, 2.

The PCR Conditions Were:

Used: 1 µl of the PCR template, 5 µl of nucleotide DIG-dUTP mix, 15 pmol each of oligonucleotide PbioS2,1 and PbioS2,2, buffer from the kit with 1.75 MM $MgCl_2$, 0.75 µl of expand polymerase mix (Boehringer Mannheim).

Amplification Conditions:

Melting of the DNA at 94° C. for 2 min, melting of the DNA at 94° C. for 10 sec, annealing at 45° C. for 30 sec, elongation at 68° C. for 3.30 min over 10 cycles, melting of the DNA at 94° C. for 10 sec, annealing at 45° C. for 30 sec, elongation at 68° C. for 3.30 min, extension of the elongation for 20 sec per cycle over 20 cycles. Purification of the DIG-labeled fragment by PCR purification kit.

4. Southern Analysis of bioS2 with Chromosomal DNA

In further steps, genomic DNA was digested by restriction enzymes and analyzed by Southern hybridization using the labeled DNA probe.

Chromosomal *E. coli* DNA W3110 (10 µg) was completely digested with the following restriction enzymes: EcoRI, BamHI, Acc65I, HindIII, SalI. The volume of the mixtures was 50 µl, and the amount of each enzyme was 30 U. The mixtures were incubated for 4 h. The DNA digested in this way was fractionated through a 1% agarose gel in TBE buffer (Sambrook, J. Fritsch, E F. Maniatis, T. 2nd ed. Cold Spring Harbor Laboratory Press., 1989, ISBN 0-87969-373-8) and transferred with the aid of a pressure transfer chamber (Stratagene) to a nylon membrane (Boehringer Mannheim) and covalently fixed to the membrane by UV irradiation (Stratalinker, Stratagene). The hybridization with the DIG-labeled DNA probe took place in DIG Easyhyb buffer (Boehringer Mannheim) at 65° C. for 15 h. Development of the blot in accordance with the manufacturer's instructions shows hybridization of the BioS2 DIG-DNA probe with bands whose sizes were determined to be about 3–4 kb in the case of Acc65I, EcoRI and HindIII. BamHI-digested DNA showed hybridization with the bioS2 probe with a fragment of a considerably higher molecular weight. 3–4 kb fragments were preferably used for further cloning.

Cloning of bioS2 by Inverse PCR

In the case of the EcoRI digestion, a fragment of about 4 kb which harbors the gene which is sought was identified. The complete gene was then amplified and cloned by the inverse PCR technique. In the first step of the inverse PCR, chromosomal *E. coli* DNA was completely digested by EcoRI. In the second step, the EcoRI-digested DNA was then covalently ligated at low DNA concentrations (about 20 ng/ml) from the previously described restriction digestion by ligase under conditions under which, viewed statistically, there is intramolecular linkage. In the third step, a PCR was then carried out employing oligonucleotides whose sequence is specific for the target gene which is sought.

Specifically amplified DNA segments can be identified on the basis of their size, which emerges from the size of the restriction fragment from the Southern analysis and from the localization of the oligonucleotides in the known section of the gene. Fragments identified in this way are then cloned into a suitable vector such as pBS SK Bluescript/pCR Script (Stratagene), and sequenced.

Experimental Procedure:

1 μg of chromosomal DNA from the strain W3110 was completely digested by 15 U of EcoRI (Boehringer Mannheim) in a volume of 50 μl. The completeness of digestion was checked by loading 30 μl onto an agarose gel. Fragments from this digestion of chromosomal DNA (10 μl of the digest=200 ng) were incubated in a volume of 100 μl together with 10 μl of ligation buffer and 2 U of T4 ligase (Boehringer Mannheim) at 15° C. for 15 h (intramolecular ligation reaction). After the ligation reaction, the T4 ligase was inactivated by incubation at 65° C. for 20 min. 5 μl of this ligation mixture were used as template for a PCR. The primers PbioS2,3 (5'-GCGTGGGTAAACTGCCTATCGACCTGAGCC-3') (SEQ ID NO:33) and PbioS2,4 (5'-CTACGCTTCCTTCAGCCTGCCAGCCGAAA-3') (SEQ ID NO:34) were synthesized starting from the sequence of bioS2.

Oligonucleotide PbioS2,3 hybridizes on the 5' side of bioS2 and results in the elongation of amplification of the coding sequence taking place on the 5' side on the complementary strand in the 3' direction.

Oligonucleotide PbioS2,4 hybridizes on the 3' side of bioS2 and results in the elongation of amplification of the coding sequence taking place on the 3' side on the coding strand in the 3' direction.

Used: 5 μl of the ligation mixture, 1.75 μl of deoxynucleotide mixture (350 μmol, Boehringer Mannheim), 15 pmol of each oligonucleotide PbioS2,5 and PbioS2,6, buffer 1 from the kit with 1.75 mM $MgCl_2$, 0.75 μl of expand polymerase mix.

Conditions for the amplification of the ligated *E. coli* DNA with primer PbioS2,3/PbioS2,4. Expand kit (Boehringer Mannheim) melting of the DNA at 94° C. for 2 min, melting of the DNA at 94° C. for 10 sec, annealing at 61° C. for 30 sec, elongation at 68° C. for 3.30 min over 10 cycles, melting of the DNA at 94° C. for 10 sec, annealing at 61° C. for 30 sec, elongation at 68° C. for 3.30 min, extension of the elongation for 20 sec per cycle over 20 cycles.

The described amplification resulted in a PCR product of about 3 kb. This DNA fragment showed pronounced Southern hybridization with the bioS2-DIG-DNA probe described above under stringent conditions.

It was assumed that this DNA fragment comprises DNA sequences which are highly homologous with bioS2. This DNA fragment was therefore cloned into a vector in order to characterize it further and sequence it. Using the pCR Script kit (Stratagene), the DNA fragment was first treated with Pfu polymerase in accordance with the manufacturer's instructions, and then ligated into the vector pCR Script. The ligation mixture was transformed into XL1-blue cells (Stratagene) and plated out on LB-Amp. A positive clone which harbored a fragment was identified by miniperparation analysis. Sequencing revealed the complete sequence depicted in SEQ ID No. 3 (=bioS2).

BioS2 was then amplified and cloned as expression cassette as for bioS1. For this purpose, an MluI recognition site and an optimized Shine-Dalgarno sequence were added on the 5' side of the gene, and an MluI recognition site was added on the 3' side of the gene, by PCR with the oligonucleotides PbioS2,5 (5'-CATGACGCGTAAAGAGGAGAAATTAACTATGA ATTACCGATTTATTTGG-3') (SEQ ID NO:35) and PbioS2,6 (5'-GCGACGCGTGATTAATGATGAGCCCAT-3') (SEQ ID NO:36).

PCR Procedure:

0.5 μg of chromosomal DNA from W3110 was employed as template. The oligonucleotides PbioS2,5 and PbioS2,6 were each employed in a concentration of 15 pM. The concentration of dNTPs was 200 μM. 2.5 U of Pwo DNA polymerase (Boehringer Mannheim) were employed as polymerase in the manufacturer's reaction buffer. The volume for the PCR was 100 μl.

Amplification Conditions:

Denaturation at 94° C. for 2 sec, annealing of the oligonucleotides at 55° C. for 30 sec, elongation at 72° C. for 45 sec. The PCR was carried out over 30 cycles.

The resulting DNA product with the correct size of about 1200 bp was purified by the PCR purification kit (Boehringer Mannheim) and digested by MluI in a suitable. buffer.

Figure 3:
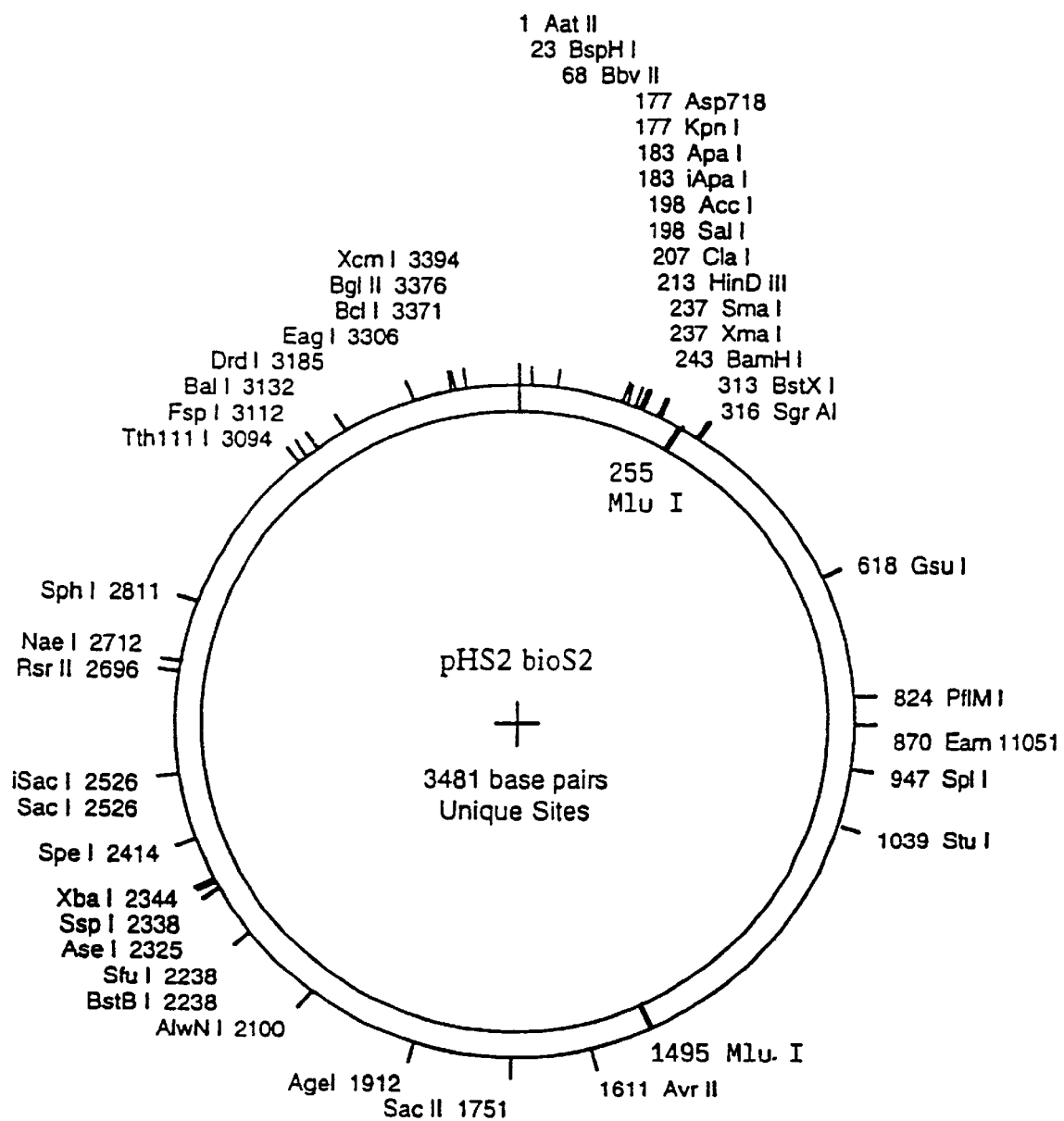
FIG. 3 is a pictorial depiction of the construct pHS2 bioS2. (SEQ ID No. 11)
Figure 4:
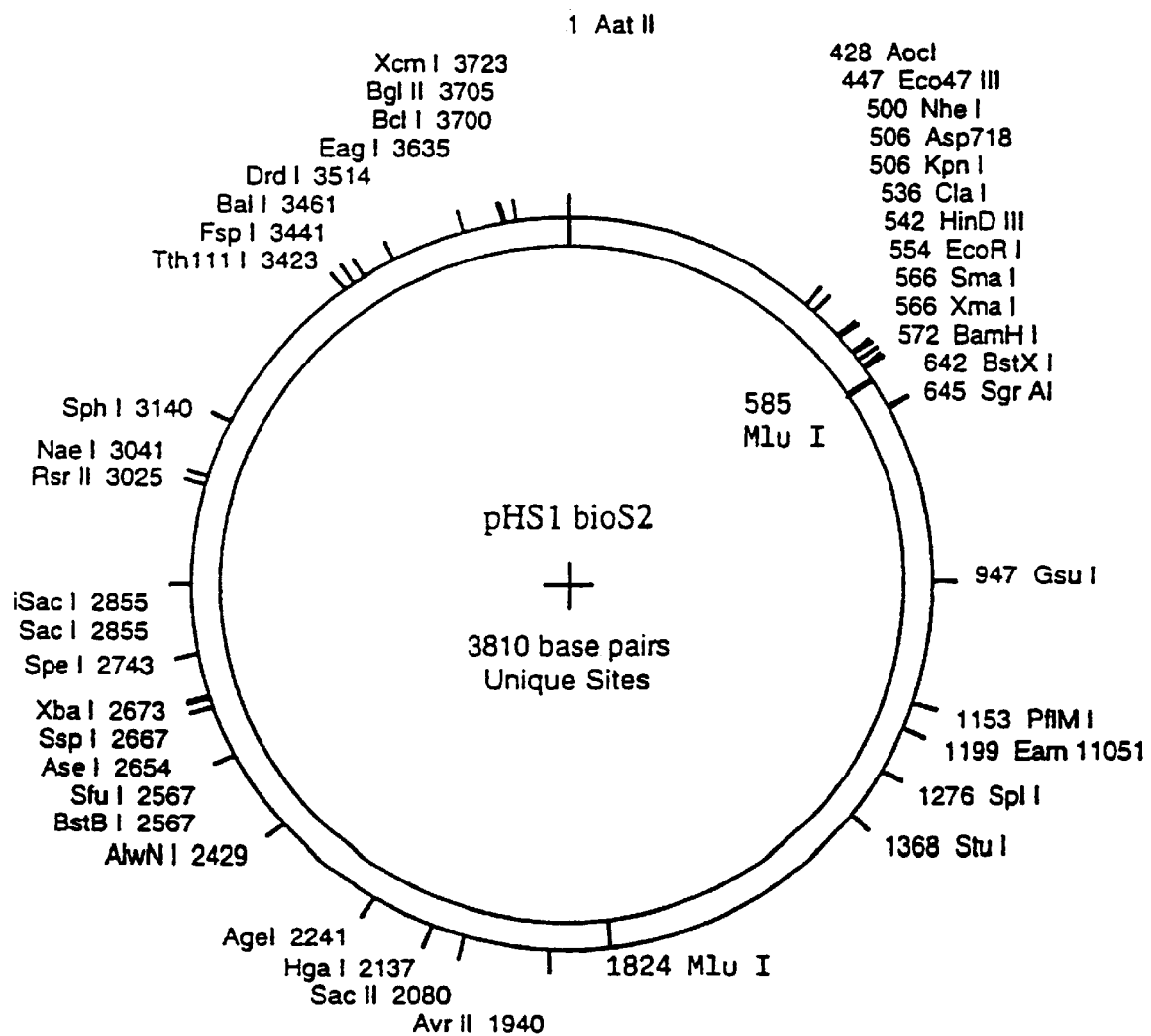
FIG. 4 is a pictorial depiction of the construct pHS1 bioS2. (SEQ ID No. 7)

5 μg of the vector pHS2 were digested by MluI and dephosphorylated by shrimp alkaline phosphatase (SAP) (Boehringer Mannheim). After denaturation of the SAP, the vector and fragment were ligated in a molar ratio of 1:3 by the rapid DNA ligation kit in accordance with the manufacturer's instructions. The ligation mixture was transformed into the strain XL1-blue. Positive clones were identified by plasmid preparation and restriction analysis. Correct orientation of the bioS2 fragment in pHS2 was determined by restriction digestion and sequencing. The vector was called pHS2 bioS2 (FIG. 3). The sequence of pHS2 bioS2 is to be found in SEQ ID No. 11. The derived amino acid sequence of bioS2 in the vector is to be found in SEQ ID No. 12. Cloning of bioS2 into the vector pHS1 was carried out in a similar way. The sequence of pHS1 bioS2 is to be found in SEQ ID No. 7 (FIG. 4). The derived amino acid sequence of bioS2 in the vector is to be found in SEQ ID No. 8.

5. Construction of the plasmid pHBbio14

The Bio operon was cloned in vivo by a transducing lambda phage. Lambda bio⁺phages were selected by transduction of an *E. coli* bio-negative strain to bio⁺. The isolated bio⁺ transducing lambda phage was propagated, and the lambda DNA was purified. This was followed by excision of an 8.7 kb EcoRI/HindIII fragment with the complete biotin operon out of the lambda phage DNA and ligation of the fragment into pBR322 which had been cut with EcoRI/HindIII. Positive clones were identified by plasmid preparation and restriction analysis.

Deletion of a 1.2 kb 3' Fragment of bioD

Unnecessary gene sequences on the 3' side of the bioD gene were deleted. For this purpose, an EcoRI cleavage site was introduced behind the bioD stop codon by PCR. The oligonucleotides Pbio1,1 (5'-AATAAGGAATTCTTATGTACTTTCCGGTTGCCG-3') (SEQ ID NO:37) and Pbio1,2 (5'-AACAGCAGCCTGCAGCTGGATTA-3') (SEQ ID NO:38) for this PCR were developed according to the operon sequence of Otsuka et al. (J. Biol. Chem. 263, 1988: 19577–85).

PCR Conditions:

2,5 U of Taq polymerase (Perkin Elmer) and 15 pmol of each primer were reacted in a volume of 100 μl. The annealing was carried out at 50° C. and the elongation at 72° C. for 1 min over 30 cycles. A 488 bp fragment was isolated and purified on an agarose gel.

Digestion of the resulting fragment with EcoRI/PstI. Digestion of pHBbio1 with EcoRI/PstI. Isolation of a 9.5 kb fragment.

The 9.5 kb fragment was ligated to the 488 bp fragment and transformed into XL1-blue cells. Resulting clones were analyzed by plasmid preparation and by restriction analysis of the plasmid DNA using the enzymes EcoRI and HindIII, and positive clones which harbored a 5.9 kb fragment were identified. A clone was isolated and was called pHBbio2. Plasmid DNA was obtained from this clone. 5 μg of pHBbio2 were digested with EcoRI/HindIII, and the 5.9 kb fragment which contained the complete biotin biosynthesis genes was isolated.

5 μg of the plasmid pAT153 were digested with EcoRI and HindIII. The resulting 5.9 kb fragment with the biotin biosynthesis genes was ligated to the digested vector pAT153 and transformed into XL1-blue. Resulting clones were analyzed by plasmid preparation and by restriction analysis of the plasmid DNA with the enzymes EcoRI and HindIII. Positive clones were identified, and a clone was isolated and called pHBbio14.

6. Increasing Biotin Productivity by Overexpression of bioS1

Strain BM4092 (Barker and Campbell) was transduced to recA⁻ by a P1 transduction using a P1 lysate which had grown on a recA::Tn10-harboring strain. Success of the transduction was detected by increased UV sensitivity of the positive transductants. The resulting strain LU8091 was then transformed with the plasmid pHBbio14 by the $CaCl_2$ method and was cultured on LB-ampicillin 100 μg/ml. One clone was isolated, and this was transformed with each of the plasmids pHS1 bioS1 and pHS2 bioS2 by the $CaCl_2$ method and selected on LB agar, ampicillin 100 μg/ml and kanamycin 25 μg/ml.

One colony of each of the transformants was inoculated in a DYT culture with the appropriate antibiotic and incubated for 12 h. The overnight culture was employed for inoculation of a 10 ml culture in TB medium (Sambrook, J. Fritsch, E F. Maniatis, T. 2nd ed. Cold Spring Harbor Laboratory Press., 1989 ISBN 0-87969-373-8) with the appropriate antibiotics, and was cultured for 24 h. After completion of growth, the cells were removed from the culture supernatant by centrifugation, and the biotin and dethiobiotin concentrations were determined by an ELISA with streptavidin and avidin in the supernatant. The results of this determination are to be found in Table I.

TABLE I

Determination of the biotin and dethiobiotin concentrations

| Strain | Plasmid I | Plasmid II | Biotin mg/l | Dethiobiotin mg/l |
|---|---|---|---|---|
| Lu8091 | pHBbio14 | | 9.4 | 45.6 |
| Lu8091 | pHBbio14 | pHS1 bioS1 | 15.3 | 19.7 |
| Lu8091 | pHBbio14 | pHS2 bioS1 | 19.2 | 15.8 |

We claim:

1. A process for preparing biotin, which comprises expressing a biotin synthase gene selected from the group consisting of sequences SEQ ID NO: 1 and SEQ ID NO: 3 in a prokaryotic or eukaryotic host organism able to synthesize dethiobiotin.

2. A process as claimed in claim 1, wherein the expression of the biotin synthase gene as set forth in claim 1 leads to an increased conversion of dethiobiotin into biotin.

3. A process as claimed in claim 1, wherein the host organism used is an organism selected from the group of genera Escherichia, Citrobacter, Serratia, Klebsiella, Salmonella, Pseudomonas, Comamonas, Acinetobacter, Azotobacter, Chromobacterium, Bacillus, Clostridium, Arthrobacter, Corynebacterium, Brevibacterium, Lactococcus, Lactobacillus, Streptomyces, Rhizobium, Agrobacterium, Staphylococcus, Rhodotorula, Sporobolomyces, Yarrowia, Schizosaccharomyces or Saccharomyces.

4. A process as claimed in claim 1, wherein said host organism has no or only very diminished natural regulation of biotin synthesis such that said organism has a considerably higher than natural biotin productivity.

5. A gene construct comprising a biotin synthase gene selected from the group of sequences consisting of SEQ ID NO:1 and SEQ ID NO:3, which is functionally linked to sequences selected from the group consisting of one or more heterologous regulatory sequences and a genetically modified natural regulatory sequence, where the natural regulation by biotin has been switched off.

6. A gene construct as claimed in claim 5, which has been inserted in a vector which is suitable for the expression of the gene in a prokaryotic or eukaryotic host organism.

7. An organism selected from the group consisting of bacteria, fungi, yeasts and plants comprising a gene construct as claimed in claim 5.

* * * * *